(12) United States Patent
Ahmed et al.

(10) Patent No.: US 7,977,337 B2
(45) Date of Patent: Jul. 12, 2011

(54) QUINOLINE DERIVATIVES AND THEIR USE AS 5-HT6 LIGANDS

(75) Inventors: Mahmood Ahmed, Harlow (GB); Christopher Norbert Johnson, Harlow (GB); Martin C Jones, Harlow (GB); Gregor James MacDonald, Harlow (GB); Stephen Frederick Moss, Harlow (GB); Mervyn Thompson, Harlow (GB); Charles Edward Wade, Stevenage (GB); David R Witty, Harlow (GB)

(73) Assignee: Glaxo Group Limited, Greenford, Middlesex (GB)

(*) Notice: Subject to any disclaimer, the term of this patent is extended or adjusted under 35 U.S.C. 154(b) by 0 days.

(21) Appl. No.: 12/847,039

(22) Filed: Jul. 30, 2010

(65) Prior Publication Data

US 2010/0305107 A1    Dec. 2, 2010

Related U.S. Application Data

(63) Continuation of application No. 12/541,456, filed on Aug. 14, 2009, now Pat. No. 7,799,774, which is a continuation of application No. 12/205,079, filed on Sep. 5, 2008, now Pat. No. 7,601,837, which is a continuation of application No. 10/509,078, filed as application No. PCT/EP03/03197 on Mar. 25, 2003, now Pat. No. 7,452,888.

(30) Foreign Application Priority Data

Mar. 27, 2002 (GB) .................................. 0207289.0
Nov. 4, 2002 (GB) .................................. 0225678.2

(51) Int. Cl.
*A61K 31/47* (2006.01)
*A61K 31/496* (2006.01)

(52) U.S. Cl. ................... 514/253.02; 514/218
(58) Field of Classification Search .................. None
See application file for complete search history.

(56) References Cited

U.S. PATENT DOCUMENTS

| | | | |
|---|---|---|---|
| 5,576,338 A | 11/1996 | Friesen et al. | |
| 5,596,001 A | 1/1997 | Hamanaka | |
| 6,172,084 B1 | 1/2001 | Cuny et al. | |
| 6,187,805 B1 | 2/2001 | Pineiro et al. | |
| 6,207,679 B1 | 3/2001 | Cuny et al. | |
| 6,310,212 B1 | 10/2001 | Yuan et al. | |
| 6,316,450 B1 | 11/2001 | Bromidge et al. | 514/253.05 |
| 6,376,670 B1 | 4/2002 | Cuny et al. | |
| 6,380,199 B1 | 4/2002 | Reavill et al. | |
| 6,403,808 B1 | 6/2002 | Glennon et al. | 548/491 |
| 6,489,488 B2 | 12/2002 | Glennon et al. | 548/439 |
| 6,518,297 B2 | 2/2003 | Glennon et al. | 514/415 |
| 6,548,504 B1 | 4/2003 | Bromidge et al. | 514/252.12 |
| 6,787,535 B2 | 9/2004 | Beard et al. | |
| 6,849,644 B2 | 2/2005 | Bromidge et al. | 514/307 |
| 7,084,169 B2 | 8/2006 | Zhao | 514/418 |
| 7,087,750 B2 | 8/2006 | Caldirola et al. | 540/575 |
| 7,098,233 B2 | 8/2006 | Di Cesare et al. | 514/415 |
| 7,262,188 B2 | 8/2007 | MacDonald et al. | 514/218 |
| 7,452,888 B2 | 11/2008 | Ahmed et al. | 514/253.07 |
| 7,601,837 B2 | 10/2009 | Ahmed et al. | 544/363 |
| 2001/0051719 A1 | 12/2001 | Bromidge et al. | 544/56 |
| 2003/0144505 A1 | 7/2003 | Bromidge et al. | 544/59 |
| 2004/0024210 A1 | 2/2004 | Johansson et al. | |
| 2004/0034036 A1 | 2/2004 | Bromidge et al. | 514/255.03 |
| 2004/0132742 A1 | 7/2004 | Bromidge et al. | 514/255.03 |
| 2004/0167030 A1 | 8/2004 | Berontas et al. | |
| 2005/0090485 A1 | 4/2005 | Bromidge et al. | 514/217.01 |
| 2005/0090496 A1 | 4/2005 | Ahmed et al. | 514/248 |
| 2005/0176705 A1 | 8/2005 | Bromidge | 514/232.5 |
| 2005/0176759 A1 | 8/2005 | Ahmed et al. | 514/310 |
| 2006/0287334 A1 | 12/2006 | Johnson et al. | 514/253.07 |
| 2007/0027139 A1 | 2/2007 | Johnson et al. | 514/218 |
| 2007/0032504 A1 | 2/2007 | Gladwin | 514/253.07 |
| 2007/0191345 A1 | 8/2007 | Ahmed et al. | 514/217.07 |
| 2007/0249603 A1 | 10/2007 | Johnson et al. | 514/235.2 |
| 2007/0275979 A1 | 11/2007 | Macdonald et al. | 514/255.03 |

FOREIGN PATENT DOCUMENTS

CA    2169231 A1    8/1996
(Continued)

OTHER PUBLICATIONS

Mitchell et al., *Pharmacol.& Therapeutics*, 108: 320-333 (2005).
Chuang et al., *Alzheimer's & Dementia, The Journal of the Alzheimer's Association*, 2(3/Supp. 1):S631-S632 (2006).
London Stock Exchange Announcement—GlaxoSmithKline (GSK) plc, Issued on Thursday, Dec. 13, 2007, New York, New York.
A Dose Ranging Study to Investigate the Efficacy and Safety of SB-742457 in Alzheimer's Disease. NCT ID No. NCT00224497 (Verified 2007).
SB-742457 and Donepezil in Alzheimer's Disease. NCT ID No. NCT00348192 (2006).
Garcia-Alloza et al. *Neuropsychopharmacology*, 29: 410-416 (2004).

(Continued)

Primary Examiner — Emily Bernhardt
(74) Attorney, Agent, or Firm — Kathryn L. Sieburth; John Lemanowicz

(57) ABSTRACT

Disclosed are quinoline compounds having affinity for the 5-$HT_6$ receptor and having the formula:

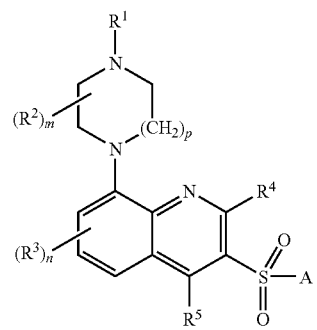

where $R^1$, $R^2$, $R^3$, $R^4$, $R^5$, n, m, p and A are defined herein, and salts thereof, compositions containing these compounds and salts and processes for making and using the same.

10 Claims, 6 Drawing Sheets

FOREIGN PATENT DOCUMENTS

| | | |
|---|---|---|
| EP | 0 605 981 | 2/1996 |
| EP | 0 818 449 | 1/1998 |
| EP | 0 631 176 | 12/2000 |
| EP | 0 867 477 | 5/2002 |
| GB | 2341549 A | 3/2000 |
| JP | 02262627 | 10/1990 |
| WO | WO 95/11592 | 5/1995 |
| WO | WO 97/32858 | 9/1997 |
| WO | WO 98/27081 | 6/1998 |
| WO | WO 98/47874 | 10/1998 |
| WO | WO 98/54157 | 12/1998 |
| WO | WO 98/54158 | 12/1998 |
| WO | WO 98/57931 | 12/1998 |
| WO | WO 98/57952 | 12/1998 |
| WO | WO 99/42465 | 8/1999 |
| WO | WO 99/47516 | 9/1999 |
| WO | WO 99/65906 | 12/1999 |
| WO | WO 99/65906 A1 | 12/1999 |
| WO | WO 00/12073 | 3/2000 |
| WO | WO 00/13681 | 3/2000 |
| WO | WO 00/34265 | 6/2000 |
| WO | WO 00/42026 | 7/2000 |
| WO | WO 00/58303 | 10/2000 |
| WO | WO 00/58313 | 10/2000 |
| WO | WO 00/63203 | 10/2000 |
| WO | WO 00/63203 A1 | 10/2000 |
| WO | WO 00/64877 | 11/2000 |
| WO | WO 01/16108 | 3/2001 |
| WO | WO0117963 A2 | 3/2001 |
| WO | WO 01/32646 | 5/2001 |
| WO | WO 01/32660 | 5/2001 |
| WO | WO 01/40217 | 6/2001 |
| WO | WO0198279 A2 | 12/2001 |
| WO | WO 02/08178 | 1/2002 |
| WO | WO 02/20489 | 3/2002 |
| WO | WO 02/28837 | 4/2002 |
| WO | WO 02/36562 | 5/2002 |
| WO | WO 02/44170 | 6/2002 |
| WO | WO 02/089811 A1 | 11/2002 |
| WO | WO 02/098857 | 12/2002 |
| WO | WO 02/102774 | 12/2002 |
| WO | WO 03/011284 | 2/2003 |
| WO | WO 03/013510 | 2/2003 |
| WO | WO03014097 A1 | 2/2003 |
| WO | WO 03020707 A1 | 3/2003 |
| WO | WO 03/037872 | 5/2003 |
| WO | WO 03/066056 | 8/2003 |
| WO | WO 03/072558 | 9/2003 |
| WO | WO 03/080608 | 10/2003 |
| WO | WO03095434 A1 | 11/2003 |
| WO | WO 2004/000828 | 12/2003 |
| WO | WO03104193 A1 | 12/2003 |
| WO | WO2004026830 A1 | 4/2004 |
| WO | WO2004026831 A1 | 4/2004 |
| WO | WO2004035047 A1 | 4/2004 |
| WO | WO2004041792 A1 | 5/2004 |
| WO | WO 2004050085 A1 | 6/2004 |
| WO | WO2004078176 A1 | 9/2004 |
| WO | WO2004080969 A1 | 9/2004 |
| WO | WO 2005/021530 | 3/2005 |
| WO | WO 2006/038006 | 4/2006 |
| WO | WO 2007/039219 | 4/2007 |
| WO | WO 2007/039220 | 4/2007 |
| WO | WO 2007/039238 | 4/2007 |

OTHER PUBLICATIONS

Davies et al., *Drugs of the Future*, 30(5): 479-495 (2005).
Boes et al. *Eur. J. Med. Chem.*, 36(2): 165-178 (2001).
Hirst et al. *Mol. Pharmacol.*, 64: 1295-1308 (2003).
Sleight et al. *Br. J. Pharmacol.*, 124(3): 556-562 (1998).
Lindner et al. *J. Pharmacol. Exp. Ther.*, 307(2): 682-691 (2003).
Riemer et al. *J. Med. Chem.*, 46(7): 1273-1276 (2003).
Chang-Fong et al. *Bioorg. Med. Chem. Lett.*, 14(8): 1961-1964 (2004).
Glennon et al. *J. Med. Chem.*, 43(5): 1011-1018 (2000).
Russell et al., *J. Med.Chem.*, 44(23): 3881-3895 (2001).
Pineiro-Nunez et al. $229^{th}$ *ACS Natl. Mtg.*, Mar. 13-17, San Diego, Abst. Medi 282 (2005).
Stadler et al. $37^{th}$ *IUPAC Cong.* Aug. 14-19, Berlin, Abst MM-7 (1999).
Holenz et al. *J. Med. Chem.*, 48(6): 1781-1795 (2005).
Ahmed et al. *Bioorganic & Medicinal Chem. Letters.*, 15: 4867-4871 (2005).
Bourson et al. *British Journal of Pharmacol.*, 125: 1562-1566 (1998).
Sleight et al. *British Journal of Pharmacol.*, 124: 556-562 (1998).
Bentley et al. *British Journal of Pharmacol.*, 126: 1537-1542 (1999).
Bentley et al. *British Journal of Pharmacol.*, 126 (Suppl.): 66 (1999).
Thome et al. *Journal of Neural Transmission*, 108: 1175-1180 (2001).
Bentley et al. *Journal of Psychopharmacology*, A64 (Suppl.): 255 (1997).
Foley et al. *Neuropsychopharmacology*, 29: 93-100 (2004).
Tsai et al. *Neuroscience Letters*, 276: 138-139 (1999).
Kan et al. *Neuroscience Letters*, 372: 27-29 (2004).
Bourson et al. *J. Pharmaco. & Exp. Therapeutics*, 274: 173-180 (1995).
Robichaud et al. *Annual Reports in Med. Chem.*, 36: 11-20 (2000).
Rogers et al. *Psychopharmacology*, 158: 114-119 (2001).
Bromidge et al. *Bioorg. & Med. Chem. Lett.*, 11: 55-58 (2001).
Wesolowska, et al. "Effects of the Brain-Penetrant and Selective 5-HT6 Receptor Antagonist SB-399885 in Animal Models of Anxiety and Depression". *Neuropharmacology*, 52: 1274-1283 (2007).
Glennon, et al. "2-Substituted Tryptamines: Agents with Selectivity for 5-HT6 Serotonin Receptors". *J. Med. Chem.*, 43: 1011-1018 (2000).

QUINOLINE DERIVATIVES AND THEIR USE AS 5-HT6 LIGANDS

This application is a continuation of application Ser. No. 12/541,456, filed Aug. 14, 2009, now U.S. Pat. No. 7,799,774 which is a continuation of application Ser. No. 12/205,079, filed Sep. 5, 2008, now U.S. Pat. No. 7,601,837 which is a continuation of Ser. No. 10/509,078, filed Sep. 27, 2004, now U.S. Pat. No. 7,452,888 which is a 371 of International Application No. PCT/EP03/03197, filed Mar. 25, 2003, which claims the priority of Great Britain Application Nos. 0207289.0, filed Mar. 27, 2002, and 0225678.2, filed Nov. 4, 2002.

BACKGROUND OF THE INVENTION

This invention relates to novel quinoline compounds having pharmacological activity, to processes for their preparation, to compositions containing them and to their use in the treatment of CNS and other disorders.

WO 98/27081 discloses a series of aryl sulphonamide compounds that are said to be 5-HT$_6$ receptor antagonists and which are claimed to be useful in the treatment of various CNS disorders. GB-2341549, WO 99/47516 and WO 99/65906 all disclose a series of indole derivatives that are claimed to have 5-HT$_6$ receptor affinity. JP 02262627 (Japan Synthetic Rubber Co) describes a series of substituted quinoline derivatives useful as wavelength converting elements. WO 00/42026 (Novo Nordisk) describes a series of quinoline and quinoxaline compounds for use as GLP-1 agonists.

SUMMARY OF THE INVENTION

A structurally novel class of compounds has now been found which also possess affinity for the 5-HT$_6$ receptor. The present invention therefore provides, in a first aspect, a compound of formula (I) or a pharmaceutically acceptable salt thereof:

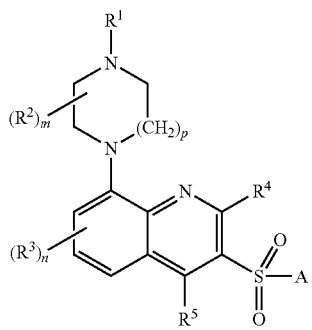

(I)

wherein:
R$^1$ and R$^2$ independently represent hydrogen or C$_{1-6}$ alkyl or R$^1$ is linked to R$^2$ to form a group (CH$_2$)$_2$, (CH$_2$)$_3$ or (CH$_2$)$_4$;
R$^3$, R$^4$ and R$^5$ independently represent hydrogen, halogen, cyano, —CF$_3$, —CF$_3$O, C$_{1-6}$ alkyl, C$_{1-6}$ alkoxy, C$_{1-6}$ alkanoyl or a group —CONR$^6$R$^7$;
R$^6$ and R$^7$ independently represent hydrogen or C$_{1-6}$ alkyl or together may be fused to form a 5- to 7-membered aromatic or non-aromatic heterocyclic ring optionally interrupted by an O or S atom;
m represents an integer from 1 to 4, such that when m is an integer greater than 1, two R$^2$ groups may instead be linked to form a group CH$_2$, (CH$_2$)$_2$ or (CH$_2$)$_3$;
n represents an integer from 1 to 3;
p represents 1 or 2;
A represents a group —Ar$^1$ or —Ar$^2$Ar$^3$;
Ar$^1$, Ar$^2$ and Ar$^3$ independently represent an aryl group or a heteroaryl group, both of which may be optionally substituted by one or more (e.g. 1, 2 or 3) substituents which may be the same or different, and which are selected from the group consisting of halogen, hydroxy, cyano, nitro, trifluoromethyl, trifluoromethoxy, C$_{1-6}$ alkyl, trifluoromethanesulfonyloxy, pentafluoroethyl, C$_{1-6}$ alkoxy, arylC$_{1-6}$ alkoxy, alkylthio, C$_{1-6}$ alkoxyC$_{1-6}$ alkyl, C$_{3-7}$ cycloalkylC$_{1-6}$ alkoxy, C$_{1-6}$ alkanoyl, C$_{1-6}$ alkoxycarbonyl, C$_{1-6}$ alkylsulfonyl, alkylsulfinyl, C$_{1-6}$ alkylsulfonyloxy, C$_{1-6}$ alkylsulfonylC$_{1-6}$ alkyl, arylsulfonyl, arylsulfonyloxy, arylsulfonylC$_{1-6}$ alkyl, C$_{1-6}$ alkylsulfonamido, C$_{1-6}$ alkylamido, C$_{1-6}$ alkylsulfonamidoC$_{1-6}$ alkyl, C$_{1-6}$ alkylamidoC$_{1-6}$ alkyl, arylsulfonamido, arylcarboxamido, arylsulfonamidoC$_{1-6}$ alkyl, arylcarboxamidoC$_{1-6}$ alkyl, aroyl, aroylC$_{1-6}$ alkyl, arylC$_{1-6}$ alkanoyl, or a group CONR$^8$R$^9$ or SO$_2$NR$^8$R$^9$, wherein R$^8$ and R$^9$ independently represent hydrogen or C$_{1-6}$ alkyl or together may be fused to form a 5- to 7-membered aromatic or non-aromatic heterocyclic ring optionally interrupted by an O or S atom;
or solvates thereof.

DETAILED DESCRIPTION OF THE INVENTION

Figure 1:
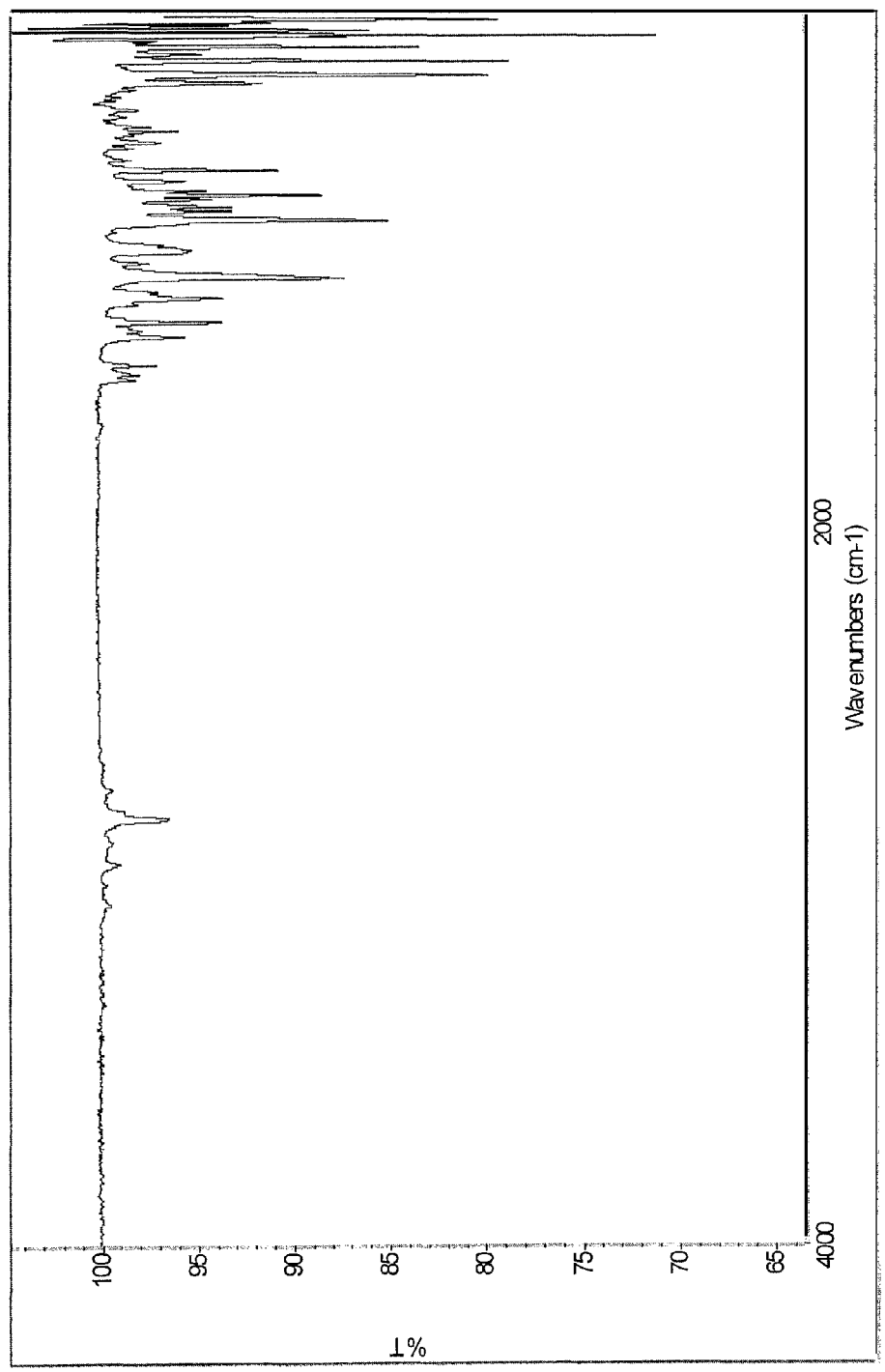
FIG. 1 shows the Infrared spectrum obtained for 3-phenylsulfonyl-8-piperazin-1-yl-quinoline (Form I).

Alkyl groups, whether alone or as part of another group, may be straight chain or branched and the groups alkoxy and alkanoyl shall be interpreted similarly. Alkyl moieties are more preferably C$_{1-4}$ alkyl, e.g. methyl or ethyl. The term 'halogen' is used herein to describe, unless otherwise stated, a group selected from fluorine, chlorine, bromine or iodine.

The term "aryl" includes phenyl and naphthyl.

The term "heteroaryl" is intended to mean a 5-7 membered monocyclic aromatic or a fused 8-10 membered bicyclic aromatic ring containing 1 to 3 heteroatoms selected from oxygen, nitrogen and sulphur. Suitable examples of such monocyclic aromatic rings include thienyl, furyl, pyrrolyl, triazolyl, imidazolyl, oxazolyl, thiazolyl, oxadiazolyl, isothiazolyl, isoxazolyl, thiadiazolyl, pyrazolyl, pyrimidyl, pyridazinyl, pyrazinyl and pyridyl. Suitable examples of such fused aromatic rings include benzofused aromatic rings such as quinolinyl, isoquinolinyl, quinazolinyl, quinoxalinyl, cinnolinyl, naphthyridinyl, indolyl, indazolyl, pyrrolopyridinyl, benzofuranyl, benzothienyl, benzimidazolyl, benzoxazolyl, benzisoxazolyl, benzothiazolyl, benzisothiazolyl, benzoxadiazolyl, benzothiadiazolyl and the like. Heteroaryl groups, as described above, may be linked to the remainder of the molecule via a carbon atom or, when present, a suitable nitrogen atom except where otherwise indicated above.

It will be appreciated that wherein the above mentioned aryl or heteroaryl groups have more than one substituent, said substituents may be linked to form a ring, for example a carboxyl and amine group may be linked to form an amide group.

Preferably, $R^1$ represents hydrogen, methyl, ethyl, isopropyl, isobutyl or 2,2-dimethylpropyl. More preferably, $R^1$ represents hydrogen or methyl, especially hydrogen.

Preferably $R^2$ represents hydrogen, methyl (e.g. 3-methyl, 2-methyl, 3,3-dimethyl or 2,5-dimethyl) or is linked to $R^1$ to form a $(CH_2)_3$ group. More preferably, $R^2$ represents hydrogen or methyl (e.g. 3-methyl), especially hydrogen.

Preferably $R^3$ represents hydrogen, methyl (e.g. 6-methyl) or halogen (e.g. 7-chloro).

More preferably, $R^3$ represents hydrogen.

Preferably $R^4$ and $R^5$ independently represent hydrogen or methyl, especially hydrogen.

Preferably n represents 1.

Preferably, m and p independently represent 1 or 2, more preferably m and p both represent 1.

In one preferred embodiment, m represents 2 and both $R^2$ groups are linked to form a $CH_2$ group linking C-2 and C-5 of the piperazine ring.

When A represents a group —$Ar^1$, $Ar^1$ preferably represents optionally substituted phenyl or pyridyl, more preferably phenyl optionally substituted with halogen (e.g. chlorine, fluorine or bromine), cyano, trifluoromethyl or trifluoromethoxy. Particularly preferred $Ar^1$ is unsubstituted phenyl or phenyl substituted by halogen (e.g. 2-chloro, 3-chloro, 4-chloro, 2-fluoro, 3-fluoro, 4-fluoro or 4-bromo), $C_{1-6}$ alkyl (e.g. 2-methyl or 4-methyl), $C_{1-6}$ alkoxy (e.g. 2-methoxy), trifluoromethyl (e.g. 2-trifluoromethyl or 3-trifluoromethyl) or trifluoromethoxy (e.g. 2-trifluoromethoxy).

When A represents a group —$Ar^2$—$Ar^3$, $Ar^2$ and $Ar^3$ preferably both independently represent phenyl or monocyclic heteroaryl group as defined above.

Preferably A represents a group —$Ar^1$.

Most preferred —$Ar^1$ is unsubstituted phenyl.

Preferred compounds according to the invention include examples E1-E43 as shown below, or a pharmaceutically acceptable salt thereof.

The compounds of formula (I) can form acid addition salts thereof. It will be appreciated that for use in medicine the salts of the compounds of formula (I) should be pharmaceutically acceptable. Suitable pharmaceutically acceptable salts will be apparent to those skilled in the art and include those described in J. Pharm. Sci., 1977, 66, 1-19, such as acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. The present invention includes within its scope all possible stoichiometric and non-stoichiometric forms.

The compounds of formula (I) may be prepared in crystalline or non-crystalline form, and, if crystalline, may optionally be solvated, e.g. as the hydrate. This invention includes within its scope stoichiometric solvates (e.g. hydrates) as well as compounds containing variable amounts of solvent (e.g. water).

Certain compounds of formula (I) are capable of existing in stereoisomeric forms (e.g. diastereomers and enantiomers) and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof.

A more preferred compound according to the invention includes 3-phenylsulfonyl-8-piperazin-1-yl-quinoline or a pharmaceutically acceptable salt thereof (e.g. as the hydrochloride salt), most preferably as the free base (e.g. 3-phenylsulfonyl-8-piperazin-1-yl-quinoline).

It has been found that the free base of 3-phenylsulfonyl-8-piperazin-1-yl-quinoline exists in more than one polymorphic form. The present invention extends to all such forms whether in a pure polymorphic form or when admixed with any other material, such as another polymorphic form. Herein, the polymorphic forms of the free base are referred to as Form I and Form II. Each of the said forms may also be referred to herein as the free base as appropriate.

Suitably, the invention provides the free base, suitably as characterised by data provided by at least one of the following: infrared, Raman, X-ray powder diffraction or nuclear magnetic resonance and melting point data as provided herein, including partial spectral data provided herein.

In a further aspect the invention provides 3-phenylsulfonyl-8-piperazin-1-yl-quinoline Form I.

In a further aspect the invention provides 3-phenylsulfonyl-8-piperazin-1-yl-quinoline Form II.

Figure 2:
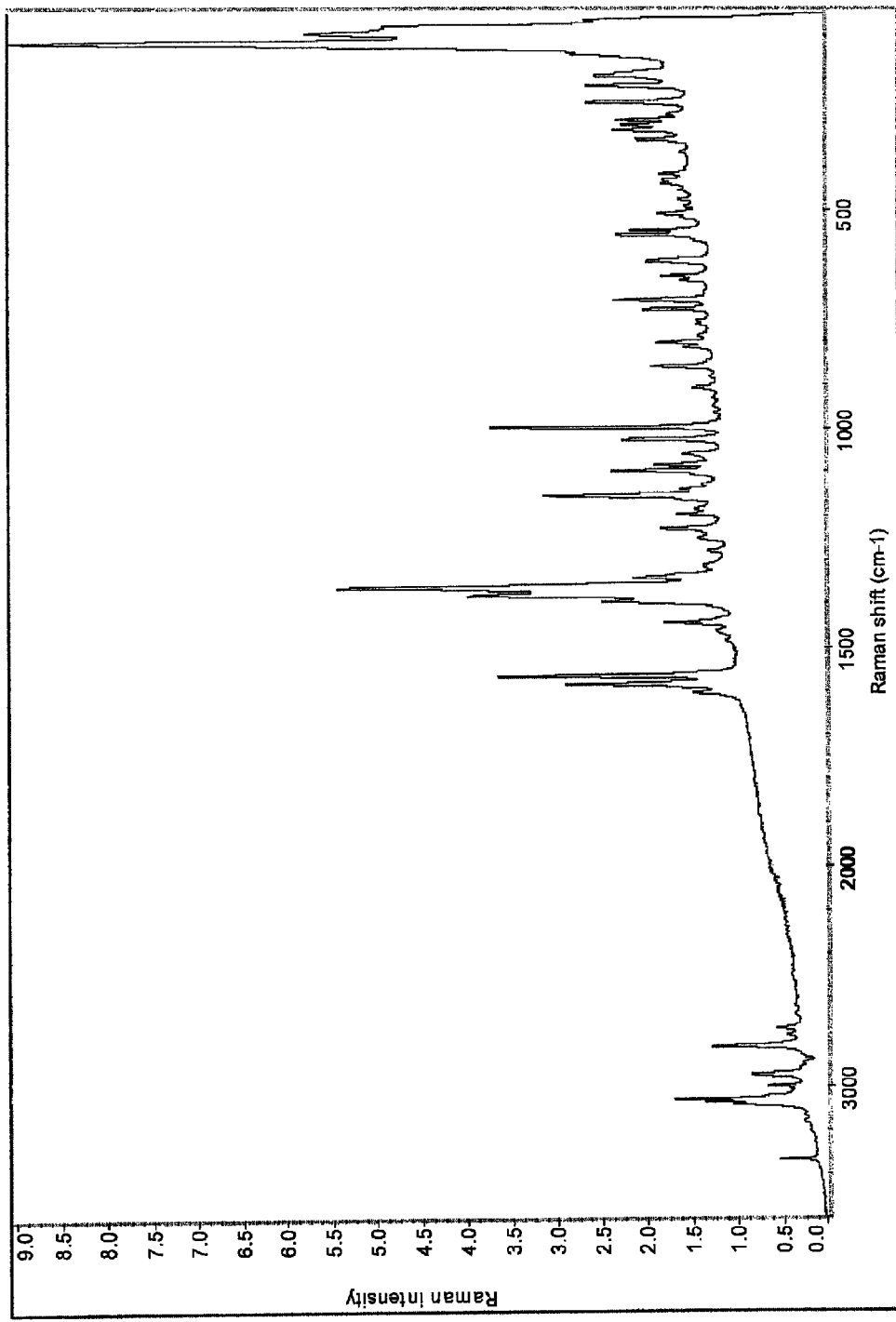
FIG. 2 shows the Raman spectrum obtained for 3-phenylsulfonyl-8-piperazin-1-yl-quinoline (Form I).
Figure 3:
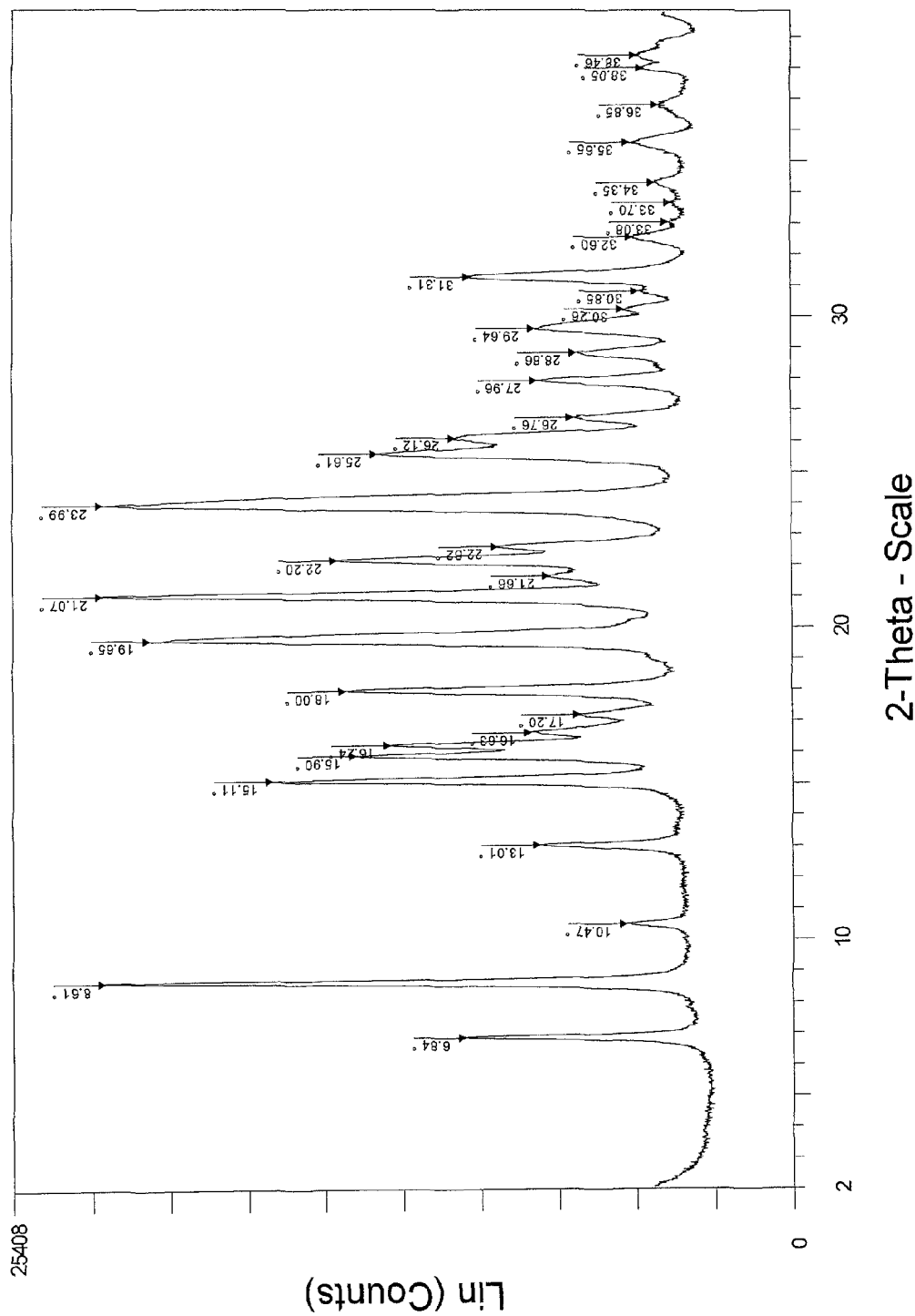
FIG. 3 shows the X-Ray Powder Diffractogram obtained for 3-phenylsulfonyl-8-piperazin-1-yl-quinoline (Form I).

In a particular aspect, the present invention provides 3-phenylsulfonyl-8-piperazin-1-yl-quinoline (Form I), characterised by
(i) an infrared spectrum substantially in accordance with FIG. 1; and/or
(ii) a Raman spectrum substantially in accordance with FIG. 2; and/or
(iii) an X-ray powder diffraction (XRPD) pattern substantially in accordance with FIG. 3.

Figure 4:
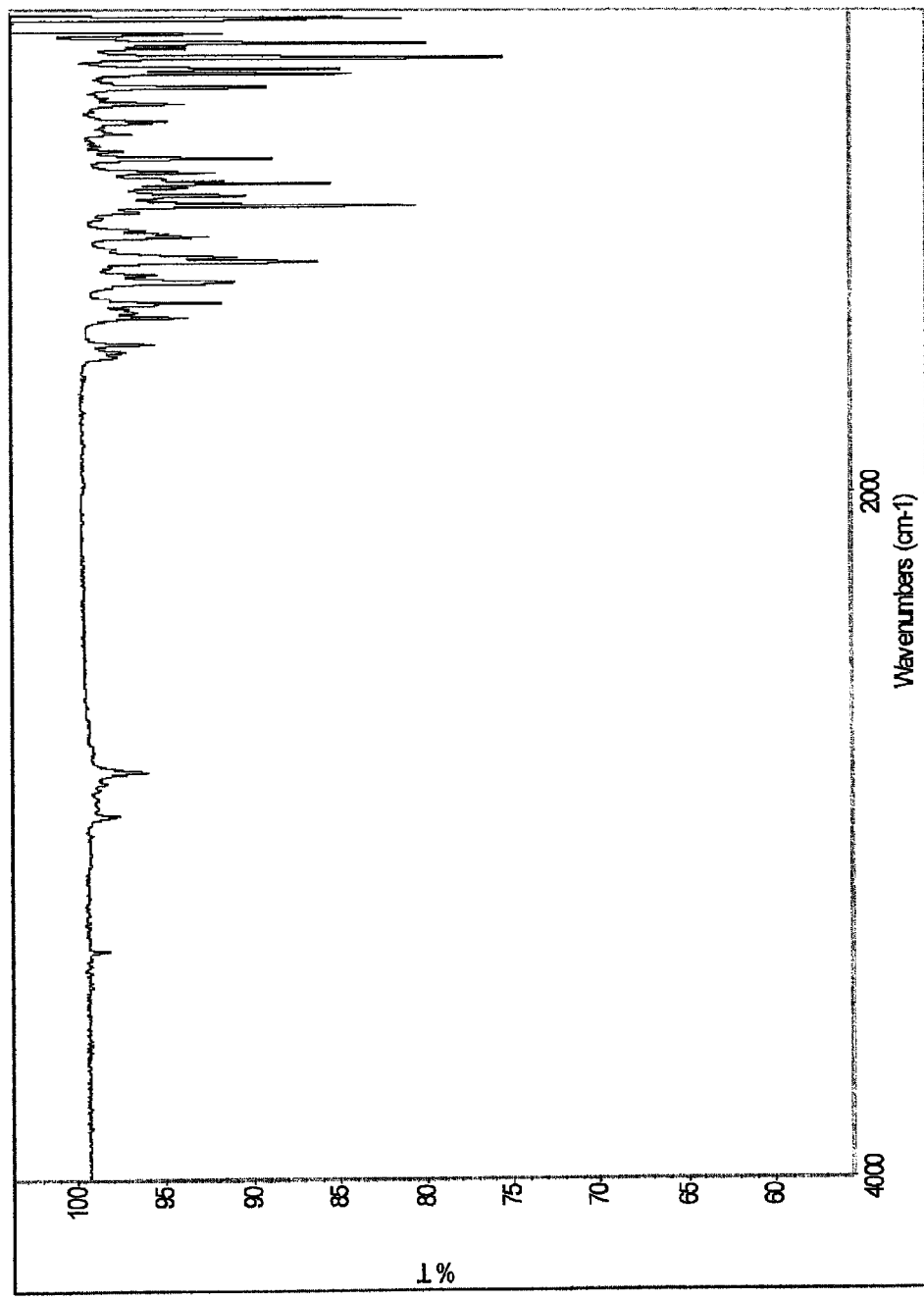
FIG. 4 shows the Infrared spectrum obtained for 3-phenylsulfonyl-8-piperazin-1-yl-quinoline (Form II).
Figure 5:
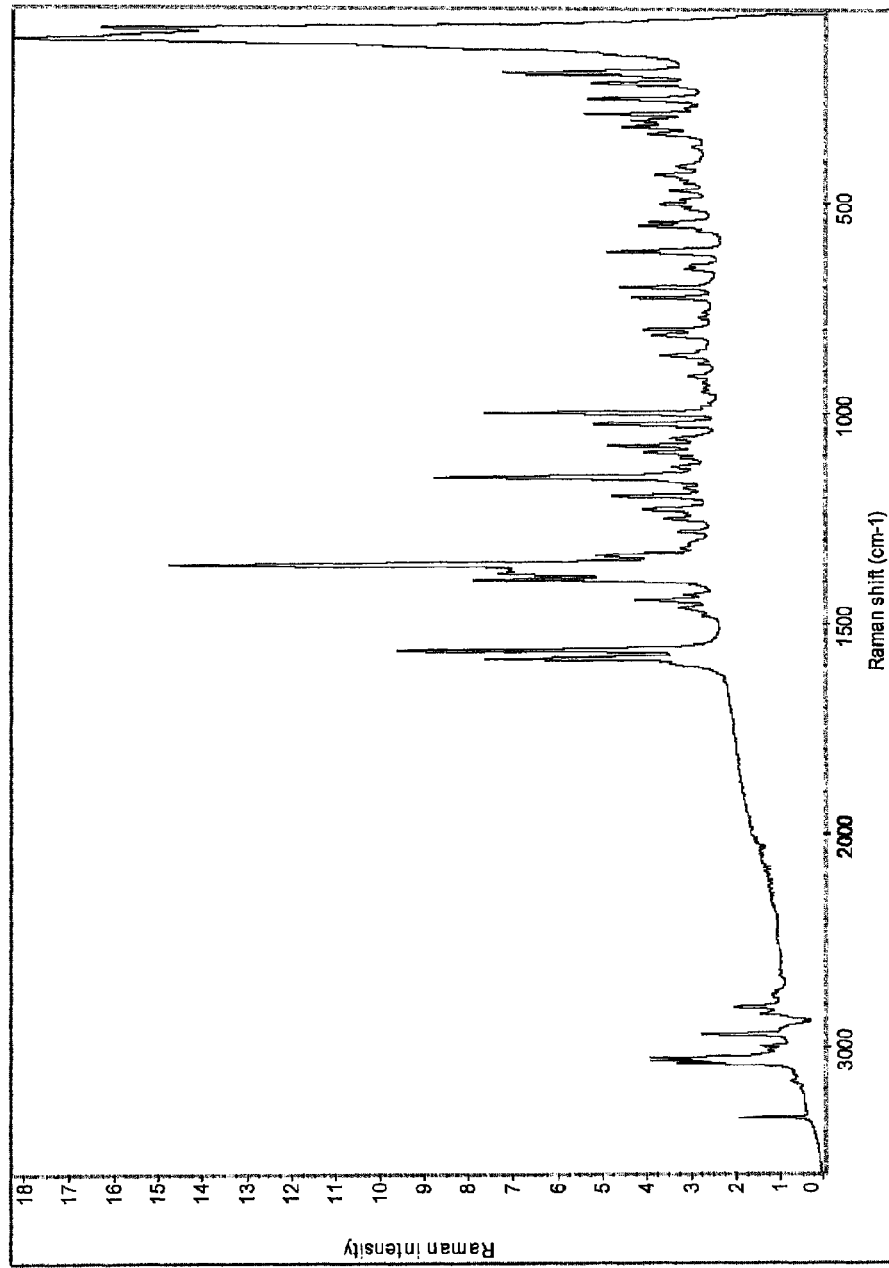
FIG. 5 shows the Raman spectrum obtained for 3-phenylsulfonyl-8-piperazin-1-yl-quinoline (Form II).
Figure 6:
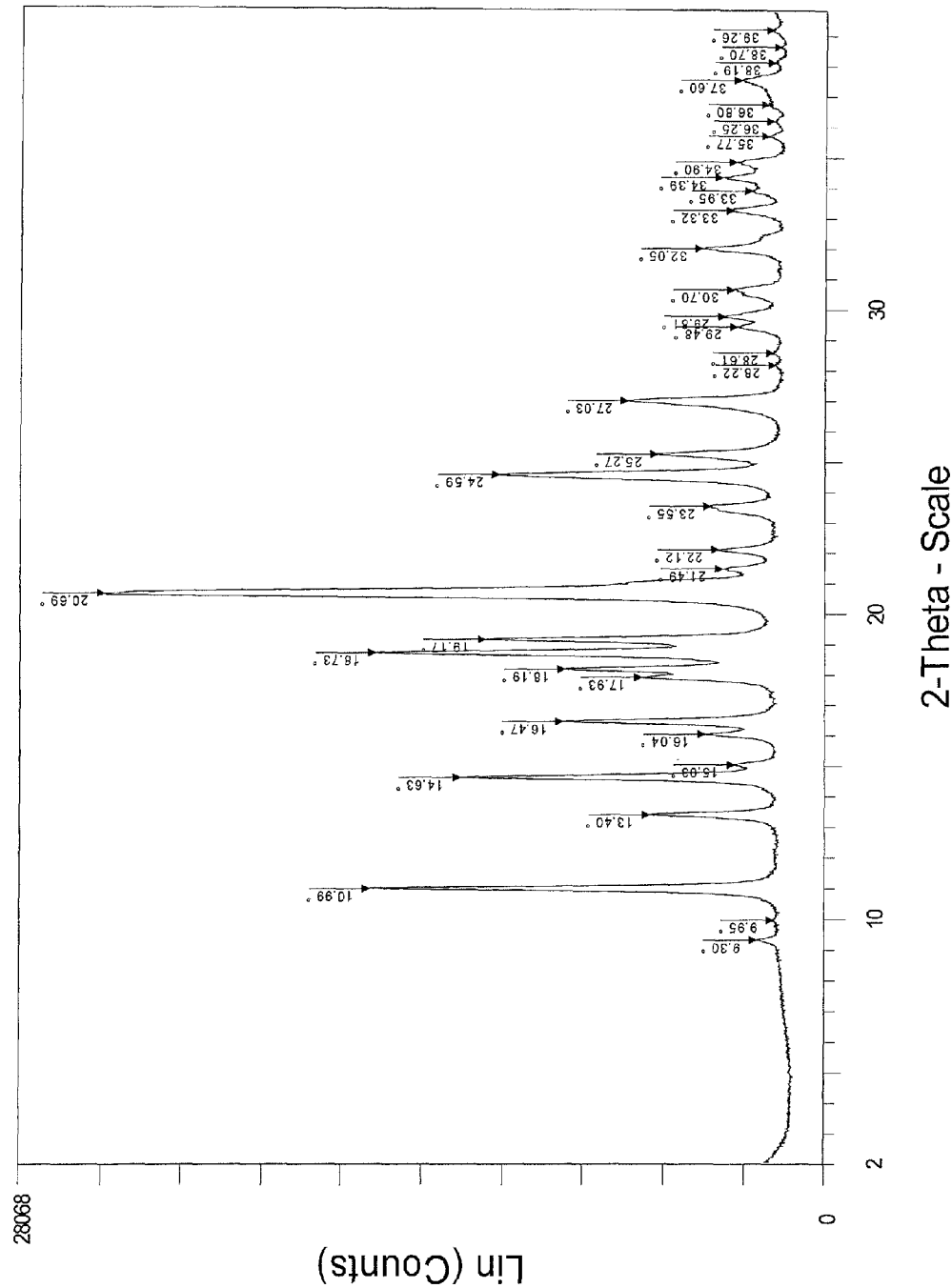
FIG. 6 shows the X-Ray Powder Diffractogram obtained for 3-phenylsulfonyl-8-piperazin-1-yl-quinoline (Form II).

In a particular aspect, the present invention provides 3-phenylsulfonyl-8-piperazin-1-yl-quinoline (Form II), characterised by
(i) an infrared spectrum substantially in accordance with FIG. 4; and/or
(ii) a Raman spectrum substantially in accordance with FIG. 5; and/or
(iii) an X-ray powder diffraction (XRPD) pattern substantially in accordance with FIG. 6.

As a consequence of greater stability provided by a higher melting point, 3-phenylsulfonyl-8-piperazin-1-yl-quinoline (Form II) is the preferred form of 3-phenylsulfonyl-8-piperazin-1-yl-quinoline.

The present invention also provides a process for the preparation of a compound of formula (I) or a pharmaceutically acceptable salt thereof, which process comprises:
(a) reacting a compound of formula (II)

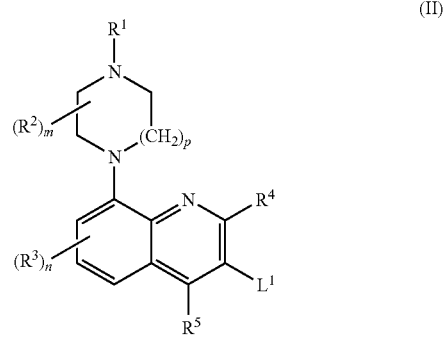

(II)

wherein $R^{1a}$ is as defined for $R^1$ or an N-protecting group, $R^2$, $R^3$, $R^4$, $R^5$, m, n and p are as defined above and $L^1$ is a leaving group such as iodo or trifluoromethylsulfonyloxy; with a compound of formula A-SO₂H, (or A-SH followed by a subsequent oxidation step) wherein A is as defined above and thereafter as necessary removing an $R^{1a}$ N-protecting group;

(b) deprotecting a compound of formula (I) which is protected; and thereafter optionally (c) interconversion to other compounds of formula (I) and/ or forming a pharmaceutically acceptable salt and/or solvate.

The present invention also provides a further process for the preparation of a compound of formula (I) or a pharmaceutically acceptable salt thereof, which process comprises:

(d) reacting a compound of formula (IV)

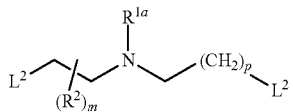
(IV)

with a compound of formula (V)

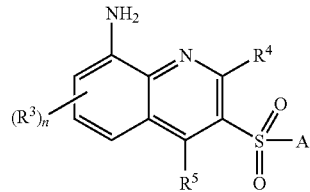
(V)

wherein $R^{1a}$, $R^2$, $R^3$, $R^4$, $R^5$, A, m, n and p are as defined above, and $L^2$ represents a suitable leaving group, such as a halogen atom and thereafter as necessary removing an $R^{1a}$ N-protecting group; or (e) reacting a compound of formula (VI)

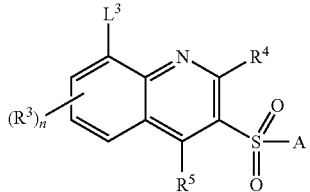
(VI)

with a compound of formula (VII)

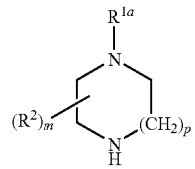
(VII)

wherein $R^{1a}$, $R^2$, $R^3$, $R^4$, $R^5$, m, n, p and A are as defined above and $L^3$ represents a suitable leaving group, such as a halogen atom (e.g. a bromine or iodine atom) or a trifluoromethylsulfonyloxy group, and thereafter as necessary removing an $R^{1a}$ N-protecting group. The N-protecting group used may be any conventional group e.g. t-butyloxy carbonyl (Boc) or benzyloxycarbonyl. Further N-protecting groups which may be used include methyl.

Process (a) wherein a compound of formula (II) is reacted with a compound of formula A-SO₂H typically comprises use of basic conditions and may be most conveniently carried out by using a suitable salt of the compound A-SO₂H (e.g. the sodium salt) in an appropriate solvent such as N,N-dimethylformamide, in the presence of a transition metal salt such as copper (I) iodide.

Process (a) wherein a compound of formula (II) is reacted with a compound of formula A-SH typically comprises use of basic conditions e.g. by using a suitable salt of the compound A-SH (e.g. the sodium salt) in an appropriate solvent such as N,N-dimethylformamide, in the presence of a suitable metal salt such as copper (I) iodide, followed by use of a suitable oxidant such as 3-chloroperbenzoic acid, peracetic acid or potassium monopersulfate.

In processes (a) and (b), examples of protecting groups and the means for their removal can be found in T. W. Greene 'Protective Groups in Organic Synthesis' (J. Wiley and Sons, 1991). Suitable amine protecting groups include sulphonyl (e.g. tosyl), acyl (e.g. acetyl, 2',2',2'-trichloroethoxycarbonyl, benzyloxycarbonyl or t-butoxycarbonyl) and arylalkyl (e.g. benzyl), which may be removed by hydrolysis (e.g. using an acid such as hydrochloric acid) or reductively (e.g. hydrogenolysis of a benzyl group or reductive removal of a 2',2',2'-trichloroethoxycarbonyl group using zinc in acetic acid) as appropriate. Other suitable amine protecting groups include trifluoroacetyl (—COCF₃) which may be removed by base catalysed hydrolysis or a solid phase resin bound benzyl group, such as a Merrifield resin bound 2,6-dimethoxybenzyl group (Ellman linker), which may be removed by acid catalysed hydrolysis, for example with trifluoroacetic acid. A further amine protecting group includes methyl which may be removed using standard methods for N-dealkylation (e.g. 1-chloroethyl chloroformate under basic conditions followed by treatment with methanol).

Process (c) may be performed using conventional interconversion procedures such as epimerisation, oxidation, reduction, reductive alkylation, alkylation, nucleophilic or electrophilic aromatic substitution, ester hydrolysis or amide bond formation. For example, N-dealkylation of a compound of formula (I) wherein $R^1$ represents an alkyl group to give a compound of formula (I) wherein $R^1$ represents hydrogen. It will be appreciated that such interconversion may be interconversion of protected derivatives of formula (I) which may subsequently be deprotected following interconversion.

In addition, process (c) may comprise, for example, reacting a compound of formula (I), wherein $R^1$ represents hydrogen, with an aldehyde or ketone in the presence of a reducing agent in order to generate a compound of formula (I) where $R^1$ represents $C_{1-6}$alkyl. This may be performed using a hydride donor agent such as sodium cyanoborohydride, sodium triacetoxyborohydride or a resin bound form of cyanoborohydride in an alcoholic solvent such as ethanol and in the presence of an acid such as acetic acid, or under conditions of catalytic hydrogenation. Alternatively, such a transformation may be carried out by reacting a compound of formula (I), wherein $R^1$ represents hydrogen, with a compound of formula $R^1$-L, wherein $R^1$ is as defined above and L represents a leaving group such as a halogen atom (e.g. bromine or iodine) or methylsulfonyloxy group, optionally in the presence of a suitable base such as potassium carbonate or triethylamine using an appropriate solvent such as N,N-dimethylformamide or a $C_{1-4}$alkanol.

Process (d) may be performed in the presence of a suitable base, such as sodium carbonate and the use of a suitable solvent such as n-butanol.

Process (e) may be performed in the presence of a palladium, nickel or copper catalyst, for example a mixture of a palladium source such as Pd$_2$(dba)$_3$ and a suitable ligand such as (R)-, (S)- or (±)-2,2'-bis(diphenylphosphino)-1,1'-binaphthyl (BINAP) or (2-dicyclohexylphosphanylphenyl)-dimethylamine or 1,1'-bis-diphenylphosphinoferrocene, together with a suitable base such as sodium t-butoxide, in an inert solvent such as 1,4-dioxane.

Compounds of formula (II) may be prepared by reacting a compound of formula (III)

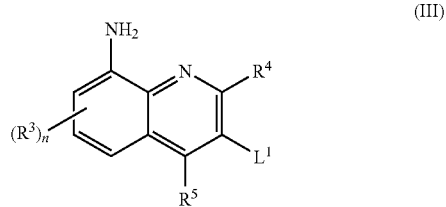

wherein $R^3$, $R^4$, $R^5$, n and $L^1$ are as defined above, with a compound of formula (IV) as defined above. This process typically comprises the use of a suitable base, such as sodium carbonate and the use of a suitable solvent such as n-butanol.

Compounds of formula (V) may be prepared in accordance with the following scheme:

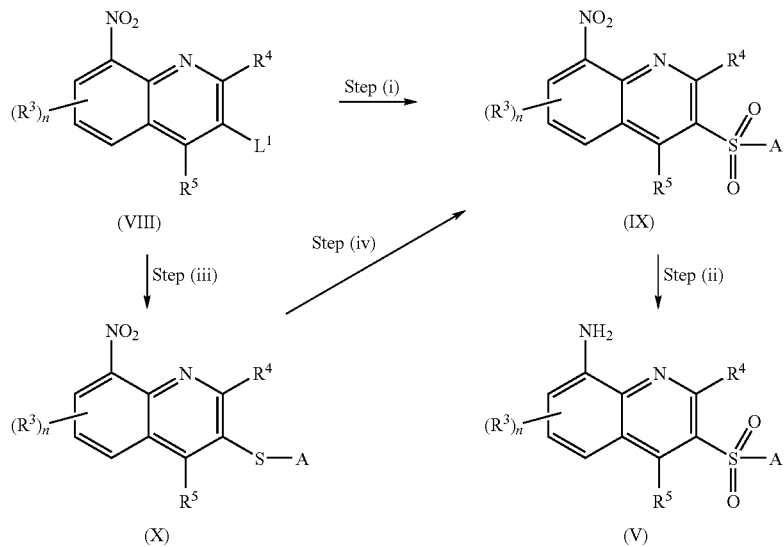

wherein $R^3$, $R^4$, $R^5$, n, A and $L^1$ are as defined above.

Step (i) typically comprises reaction of a compound of formula (VIII) with a compound of formula A-SO$_2$-M, wherein A is as defined above and M is a metal residue such as sodium or potassium, in the presence of a copper (I) salt, e.g. copper (I)triflate or copper (I) iodide, in a suitable solvent such as anhydrous N,N-dimethylformamide or 1,4-dioxane, optionally including a ligand such as N,N-dimethyl-ethylene-1,2-diamine.

Alternatively, the transformation shown in step (i) may be carried out using a two step procedure typically comprising steps (iii) and (iv).

Step (iii) typically comprises the reaction of a compound of formula (VIII) with a compound of formula A-SH, wherein A is as defined above, in the presence of a base such as sodium hydride or potassium phosphate in a suitable solvent such as anhydrous N,N-dimethylformamide or ethylene glycol, optionally in the presence of a copper (I) iodide catalyst.

Step (iv) typically comprises oxidation using a suitable oxidant such as monomagnesium peroxyphthalate, 3-chloroperbenzoic acid, peracetic acid or potassium monopersulfate.

Step (ii) typically comprises the use of a suitable reducing agent, for example titanium (III) chloride, or iron powder in an appropriate solvent system, e.g. aqueous tetrahydrofuran and/or acetic acid, respectively.

Compounds of formula (VI) wherein $L^3$ represents a halogen atom may be prepared in accordance with the following scheme:

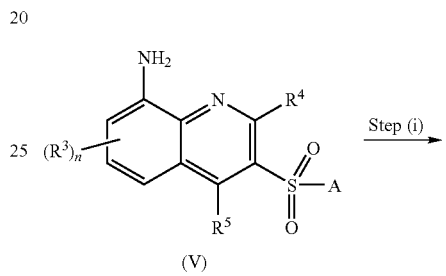

-continued

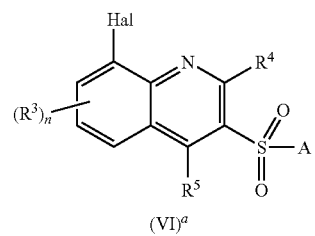

wherein $R^3$, $R^4$, $R^5$, n and A are as defined above and Hal represents a halogen atom.

Step (i) typically comprises diazotisation according to known methods (e.g. using sodium nitrite with aqueous inorganic acid as solvent, or an alkyl nitrite ester using a suitable solvent such as acetonitrile in the presence of anhydrous acid e.g. trifluoroacetic acid), followed by treatment of the resulting diazonium salt with an appropriate halide salt such as copper (I) bromide, potassium iodide or tetrabutylammonium iodide. Such a procedure may be carried out in aqueous solution or using anhydrous conditions, for example using trifluoroacetic acid as solvent.

Compounds of formula (VI) wherein $L^3$ represents a halogen atom may also be prepared in accordance with the following scheme:

disorders such as anxiety, depression, epilepsy, obsessive compulsive disorders, migraine, cognitive memory disorders (e.g. Alzheimers disease, age related cognitive decline and mild cognitive impairment), Parkinsons Disease, ADHD (Attention Deficit Disorder/Hyperactivity Syndrome), sleep disorders (including disturbances of Circadian rhythm), feeding disorders such as anorexia and bulimia, panic attacks, withdrawal from drug abuse such as cocaine, ethanol, nicotine and benzodiazepines, schizophrenia (in particular cognitive deficits of schizophrenia), stroke and also disorders associated with spinal trauma and/or head injury such as hydrocephalus. Compounds of the invention are also expected to be of use in the treatment of certain GI (gastrointestinal) disorders such as IBS (Irritable Bowel Syndrome). Compounds of the invention are also expected to be of use in the treatment of obesity.

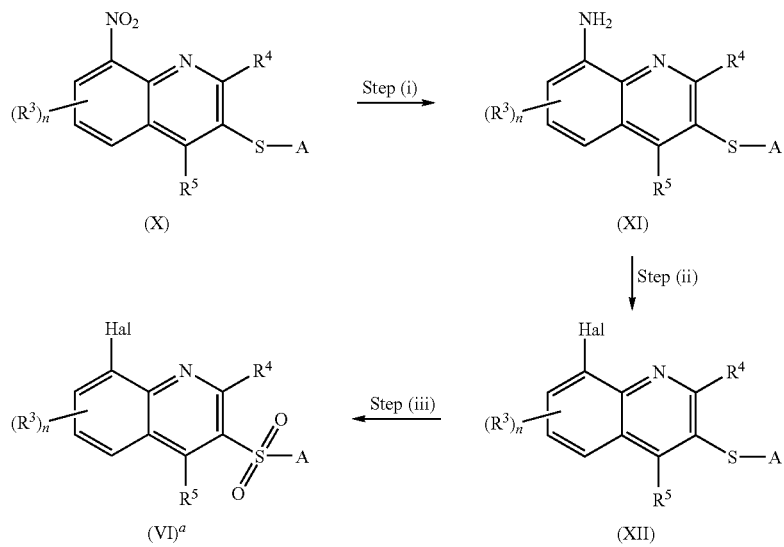

wherein $R^3$, $R^4$, $R^5$, A and n are as defined above and Hal represents a halogen atom.

Step (i) typically comprises the use of a suitable reducing agent such as iron powder, to give a compound of formula (XI).

Step (ii) typically comprises a diazotisation reaction using an aqueous or non-aqueous source of nitrosonium ions as described above, followed by conversion to a halide.

Step (iii) typically comprises the use of a suitable oxidant such as monomagnesium peroxyphthalate.

Compounds of formula (VI) wherein $L^3$ represents a trifluoromethylsulfonyloxy group may be prepared from compounds of formula (V) as defined above, by diazotisation according to known methods, followed by heating under acidic conditions, followed by treatment with trifluoromethylsulfonic anhydride in the presence of a base, such as pyridine.

Compounds of formula (III), (IV), (VII) and (VIII) are known in the literature or can be prepared by analogous methods.

Pharmaceutically acceptable salts may be prepared conventionally by reaction with the appropriate acid or acid derivative.

Compounds of formula (I) and their pharmaceutically acceptable salts have affinity for the 5-$HT_6$ receptor and are believed to be of potential use in the treatment of certain CNS Thus the invention also provides a compound of formula (I) or a pharmaceutically acceptable salt thereof, for use as a therapeutic substance, in particular in the treatment or prophylaxis of the above disorders. In particular the invention provides for a compound of formula (I) or a pharmaceutically acceptable salt thereof, for use in the treatment of depression, anxiety, Alzheimers disease, age related cognitive decline, ADHD, obesity, mild cognitive impairment, schizophrenia, cognitive deficits in schizophrenia and stroke.

The invention further provides a method of treatment or prophylaxis of the above disorders, in mammals including humans, which comprises administering to the sufferer a therapeutically effective amount of a compound of formula (I) or a pharmaceutically acceptable salt thereof.

In another aspect, the invention provides the use of a compound of formula (I) or a pharmaceutically acceptable salt thereof in the manufacture of a medicament for use in the treatment or prophylaxis of the above disorders.

5-$HT_6$ antagonists have the potential to be capable of increasing basal and learning-induced polysialylated neuron cell frequency in brain regions such as the rat medial temporal lobe and associated hippocampus, as described in International Patent Application No. PCT/EP03/00462. Thus, according to a further aspect of the present invention, we provide a method of promoting neuronal growth within the central nervous system of a mammal which comprises the step of administering a compound of formula (I) or a pharmaceutically acceptable salt thereof.

In order to use the compounds of formula (I) in therapy, they will normally be formulated into a pharmaceutical composition in accordance with standard pharmaceutical practice. The present invention also provides a pharmaceutical composition, which comprises a compound of formula (I) or a pharmaceutically acceptable salt thereof, and a pharmaceutically acceptable carrier.

A pharmaceutical composition of the invention, which may be prepared by admixture, suitably at ambient temperature and atmospheric pressure, is usually adapted for oral, parenteral or rectal administration and, as such, may be in the form of tablets, capsules, oral liquid preparations, powders, granules, lozenges, reconstitutable powders, injectable or infusable solutions or suspensions or suppositories. Orally administrable compositions are generally preferred.

Tablets and capsules for oral administration may be in unit dose form, and may contain conventional excipients, such as binding agents, fillers, tabletting lubricants, disintegrants and acceptable wetting agents. The tablets may be coated according to methods well known in normal pharmaceutical practice.

Oral liquid preparations may be in the form of, for example, aqueous or oily suspension, solutions, emulsions, syrups or elixirs, or may be in the form of a dry product for reconstitution with water or other suitable vehicle before use. Such liquid preparations may contain conventional additives such as suspending agents, emulsifying agents, non-aqueous vehicles (which may include edible oils), preservatives, and, if desired, conventional flavourings or colourants.

For parenteral administration, fluid unit dosage forms are prepared utilising a compound of the invention or pharmaceutically acceptable salt thereof and a sterile vehicle. The compound, depending on the vehicle and concentration used, can be either suspended or dissolved in the vehicle. In preparing solutions, the compound can be dissolved for injection and filter sterilised before filling into a suitable vial or ampoule and sealing. Advantageously, adjuvants such as a local anaesthetic, preservatives and buffering agents are dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilised by exposure to ethylene oxide before suspension in a sterile vehicle. Advantageously, a surfactant or wetting agent is included in the composition to facilitate uniform distribution of the compound.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 1000 mg, more suitably 0.05 to 200 mg, for example 20 to 40 mg; and such unit doses will preferably be administered once a day, although administration more than once a day may be required; and such therapy may extend for a number of weeks or months.

All publications, including but not limited to patents and patent applications, cited in this specification are herein incorporated by reference as if each individual publication were specifically and individually indicated to be incorporated by reference herein as though fully set forth.

The following Descriptions and Examples illustrate the preparation of compounds of the invention.

Description 1

3-Bromo-8-(4-methyl-piperazin-1-yl)-quinoline (D1)

bis-(2-Chloro-ethyl)-methyl-amine hydrochloride (3.7 g, 19.2 mmol) and sodium carbonate (9.0 g, 85 mmol) were added to a suspension of 3-bromo-quinolin-8-ylamine (3.9 g, 17.5 mmol) (for synthesis see Gershon et al., *Monatsh. Chem.*, 1991, 122, 935) in n-butanol (70 ml). The stirred suspension was heated at reflux for 72 h. The reaction mixture was cooled to ambient temperature, diluted with dichloromethane (300 ml) and the solution washed with water (300 ml), dried ($MgSO_4$) and concentrated in vacuo to an oil. The oil was purified by chromatography over silica gel eluting with a gradient of methanol/dichloromethane to afford the title compound (D1) as an oil (2.6 g, 8.5 mmol, 49%);

$\delta_H$ ($CDCl_3$) 2.43 (3H, s), 2.78 (4H, br s), 3.44 (4H, br, s), 7.14 (1H, d, J=6.8 Hz), 7.33 (1H, d, J=7.4 Hz), 7.47 (1H, dd, J=7.8 Hz), 8.25 (1H, d, J=2.3 Hz), 8.85 (1H, d, J=2.3 Hz).

Mass Spectrum: $C_{14}H_{16}BrN_3$ requires 305/307; found 306/308 ($MH^+$).

Description 2

3-Iodo-8-(4-methyl-piperazin-1-yl)-quinoline (D2)

A mixture of 3-bromo-8-(4-methyl-piperazin-1-yl)-quinoline (D1)(1.75 g, 5.7 mmol), copper (I) iodide (5.4 g, 28.5 mmol) and potassium iodide (9.6 g, 57.8 mmol) in hexamethylphosphoramide (20 ml) was heated in an oil bath at 150° C. for 21 h under argon. To the cooled reaction mixture was added toluene (120 ml) and 1M hydrochloric acid (120 ml) and the whole was shaken vigorously for 5 minutes. The insoluble brown solid was then collected by filtration, washed with methanol (3×40 ml) and resuspended in a mixture of dichloromethane (150 ml) and 2M sodium hydroxide (150 ml). After shaking the mixture vigorously, the insoluble material was filtered, washed with dichloromethane (2×50 ml) and discarded. The filtrate and washings were transferred to a separating funnel and the layers were separated. The aqueous phase was extracted with dichloromethane (2×100 ml) and the combined organic extracts were dried ($MgSO_4$) and concentrated to a brown oil (1.5 g) which was identified by NMR spectroscopy as a mixture of the title compound (D2) and 3-bromo-8-(4-methyl-piperazin-1-yl)-quinoline (D1) in a ratio of 4:1. This mixture was used directly in the next stage (see Example 1).

3-Iodo-8-(4-methyl-piperazin-1-yl)-quinoline (D2): $\delta_H$ ($CDCl_3$) 2.41 (3H, s), 2.76 (4H, br s), 3.42 (4H, br s), 7.14 (1H, d, J=6.8 Hz), 7.29 (1H, d, J=7.4 Hz), 7.44 (1H, dd, J=7.8 Hz), 8.47 (1H, d, J=2.3 Hz), 8.98 (1H, d, J=2.3 Hz);

Mass Spectrum: $C_{14}H_{16}IN_3$ requires 353; found 354 ($MH^+$).

Description 3

3-Iodo-8-nitroquinoline (D3)

A stirred mixture of 8-nitroquinoline (100 g, 0.57 mol) in acetic acid (500 ml) was treated with N-iodosuccinimide (155 g, 0.69 mol) portionwise over 10 minutes, and warmed to 62° C. for 6 h. A further portion of N-iodosuccinimide (25 g, 0.14 mol) was introduced and the mixture stirred for a further 16 h before cooling to ambient temperature. The solvent was removed in vacuo, keeping the temperature below 35° C. The residue was dissolved in dichloromethane (2 L) and washed successively with saturated aqueous sodium bicarbonate solution (2×1 L), 10% aqueous sodium thiosulphate solution (1 L), water (1 L), brine (100 ml), then the organic phase was dried over magnesium sulphate. The mixture was filtered and the solvent removed to give a yellow solid which was recrystallised from ethyl acetate to give the title compound (D3) (168 g, 97%) as a yellow solid;

$\delta_H$ (CDCl$_3$) 7.65 (1H, app.t), 7.94 (1H, dd), 8.07 (1H, dd), 8.66 (1H, d, J=2 Hz), 9.19 (1H, d, J=2 Hz);

Mass Spectrum: C$_9$H$_5$IN$_2$ requires 300; found 301 (MH$^+$).

Description 4

8-Nitro-3-phenylsulfonylquinoline (D4)

3-Iodo-8-nitroquinoline (D3) (135 g, 0.45 mol), was suspended in dimethylformamide (2.4 L) in a 5 L 3-necked flask fitted with an overhead stirrer, under an argon atmosphere. This mixture was treated successively with anhydrous sodium phenylsulfinate (99.6 g 0.608 mol), and bis-(copper (I)triflate)benzene complex (170 g, 0.338 mol). The resulting slurry was heated to 65° C. for 18 h. The mixture was cooled, filtered and the solvent evaporated in vacuo. Acetone (2.5 L) was added to the residue and the solution filtered. The filtrate was evaporated in vacuo, a further 2.5 L of acetone added and the mixture filtered again. The solvent was evaporated in vacuo and the residue dissolved in chloroform (3 L) and washed with 10% aqueous ammonia (2×2 L), and the organic phase was dried over magnesium sulphate and the solvent evaporated in vacuo. The dark brown residue was purified using a Biotage flash-150 chromatography apparatus (5 kg silica gel) eluting with hexane and increasing proportions of ethyl acetate to give the title compound (D4) (81.5 g, 58%) as a yellow solid;

$\delta_H$ (d6-DMSO) 7.67 (2H, t), 7.57 (1H, d, 7.96 (1H, t), 8.13 (2H, d), 8.51 (1H, d), 8.59 (1H, d), 9.42 (1H, d), 9.50 (1H, d);

Mass Spectrum: C$_{15}$H$_{10}$SO$_4$N$_2$ requires 314; found 315 (MH$^+$).

Description 5

8-Amino-3-phenylsulfonylquinoline (D5)

A slurry of 8-nitro-3-phenylsulfonylquinoline (D4) (46.7 g, 172 mmol), in tetrahydrofuran (750 ml) was added to a stirred solution of 30% titanium(III) chloride in aqueous HCl (470 ml) [Supplied by BDH] cooled in an ice bath, at such a rate that the temperature was maintained below 35° C. Once the addition was completed, the solution was stirred for a further 10 minutes then water (1.5 L) was introduced and the mixture poured into a 5 L beaker. The rapidly stirred solution was treated by portionwise addition of solid potassium carbonate in order to attain pH ~8.5. EDTA (250 g, 0.86 mol) was added and followed by further potassium carbonate to maintain pH ~8.5. The mixture was extracted with dichloromethane (3×1 L) and the combined organic phase passed through a silica plug (500 g) eluting with further dichloromethane (1 L) and 10% ethyl acetate in dichloromethane (1 L). The combined organic phases were evaporated and the residue subjected to purification using Biotage Flash-75 chromatography apparatus (2 kg silica gel), eluting with dichloromethane and increasing proportions of ether to give the title compound (D5) (34.5 g, 72%) as a pale brown solid;

$\delta_H$ (CDCl$_3$) 5.0 (2H, br s), 7.02 (1H, dd), 7.25 (1H, dd), 7.44 (1H, t), 7.50-7.59 (3H, m), 8.00-8.40 (2H, m), 8.70 (1H, s), 0.09 (1H, s);

Mass Spectrum: C$_{15}$H$_{12}$SO$_2$N$_2$ requires 284; found 285 (MH$^+$).

Description 6

8-Iodo-3-phenylsulfonylquinoline (D6)

From 8-Amino-3-phenylsulfonylquinoline (D5) in trifluoroacetic acid using n-butyl nitrite in acetonitrile followed by tetra-(n-butyl)ammonium iodide.

$\delta_H$ (CDCl$_3$) 7.39 (1H, t), 7.53-7.63 (3H, m), 7.96 (1H, d), 8.04 (2H, dd), 8.50 (1H, dd), 8.79 (1H, d), 9.32 (1H, d); Mass Spectrum: C$_{15}$H$_{10}$NO$_2$SI requires 395; found 396 (MH$^+$).

Description 7

8-(4-t-Butoxycarbonyl)piperazin-1-yl-3-phenylsulfonylquinoline (D7)

8-Iodo-3-phenylsulfonylquinoline (D6) (25.2 g, 63.6 mmol) was dissolved in dry, de-gassed dioxan (500 ml) under argon. To this solution was added sodium t-butoxide (8.56 g, 89.2 mmol) and 1-t-butyloxycarbonyl piperazine (14.2 g, 76.4 mmol) followed by a suspension of catalyst under argon. The catalyst was prepared by sonication of a mixture of tris-(dibenzylideneacetone)dipalladium(0) (1.75 g, 1.91 mmol) and 2-dicyclohexylphosphino-2'-(N,N-dimethyl amino)biphenyl (2.25 g, 5.73 mmol) in dry degassed dioxane (10 ml) for 2 minutes. This mixture was stirred at 40° C. for 5 h after which a further charge of catalyst was administered (prepared as above on half the scale) and stirring continued for 16 h at 40° C.

The mixture was filtered and the solvent removed. The residue was adsorbed onto silica and chromatographed on silica eluting with 1% methanol in dichloromethane to give the title compound (D7) (22.0 g, 76%) as a yellow solid;

$\delta_H$ (CDCl$_3$) 1.49 (9H, t), 3.31 (4H, m) 3.72 (4H, m), 7.25 (1H, m), 7.52 (2H, t), 7.57 (3H, m) 8.00 (2H, m) 8.76 (1H, d) 9.21 (1H, d);

Mass Spectrum: C$_{24}$H$_{27}$N$_3$O$_4$S requires 453; found 454 (MH$^+$).

Description 8

8-(4-t-Butoxycarbonyl)piperazin-1-yl-3-(3-trifluoromethyl)phenylsulfonylquinoline (D8)

This was prepared from 8-iodo-3-(3-trifluoromethyl)phenylsulfonylquinoline (D34) in an analogous process to that described in Description 7 (D7);

$\delta_H$ (CDCl$_3$) 1.50 (9H, s), 3.32 (4H, t), 3.73 (4H, t), 7.28 (1H, d), 7.59 (1H, s), 7.61 (1H, d), 7.69 (1H, t), 7.85 (1H, d), 8.21 (1H, d), 8.28 (1H, s), 8.79 (1H, d), 9.23 (1H, s);

Mass Spectrum: C$_{25}$H$_{26}$F$_3$N$_3$O$_4$S requires 521; found 522 (MH$^+$).

Description 9

8-(4-t-Butoxycarbonyl)homopiperazin-1-yl-3-phenylsulfonylquinoline (D9)

Prepared using an analogous process to that described in Description 7 (D7), using 8-iodo-3-phenylsulfonylquinoline (D6) (200 mg, 0.51 mmol), sodium t-butoxide (68 mg, 0.71 mmol), 1-(t-butyloxycarbonyl)homopiperazine (122 mg, 0.61 mmol), tris-(dibenzylideneacetone)dipalladium(0) (14 mg, 0.015 mmol) and 2-dicyclohexylphosphino-2'-(N,N- dimethyl amino)biphenyl (18 mg, 0.045 mmol), This resulted in the formation of a mixture containing the title compound (D9). The mixture was cooled, filtered, the solvent evaporated and the crude material was used directly in Example 14 (E14);

Mass Spectrum: $C_{25}H_{29}N_3O_4S$ requires: 467 found: 468 (MH$^+$)

Description 10

8-Amino-3-(2-chloro)phenylsulfonylquinoline (D10)

Prepared from 3-(2-chloro)phenylsulfonyl-8-nitro-quinoline (D18) in an analogous process to that described in Description 5 (D5);

$\delta_H$ (CDCl$_3$) 5.0 (2H, br s), 7.07 (1H, d), 7.27 (1H, d), 7.43-7.47 (2H, m), 7.52-7.57 (2H, m), 8.44-8.46 (1H, m), 8.77 (1H, d), 9.05 (1H, d);

Mass Spectrum: $C_{15}H_{11}ClN_2O_2S$ requires 318, 320; found 319, 321 (MH$^+$).

Description 11

8-Amino-3-(3-chloro)phenylsulfonylquinoline (D11)

Prepared from 3-(3-chloro)phenylsulfonyl-8-nitro-quinoline (D19) in an analogous process to that described in Description 5 (D5);

$\delta_H$ (CDCl$_3$) 5.0 (2H, br s), 7.05 (1H, d), 7.27 (1H, d), 7.43-7.57 (3H, m), 7.89 (1H, d), 8.00 (1H, t), 8.70 (1H, d), 9.08 (1H, d);

$C_{15}H_{11}ClN_2O_2S$ requires 318, 320; found 319, 321 (MH$^+$).

Description 12

8-Amino-3-(2-fluoro)phenylsulfonylquinoline (D12)

Prepared from 3-(2-fluoro)phenylsulfonyl-8-nitro-quinoline (D20) in an analogous process to that described in Description 5 (D5);

$\delta_H$ (CDCl$_3$) 5.1 (2H, br s), 7.08 (2H, t), 7.27 (1H, d), 7.36 (1H, t), 7.46 (1H, m), 7.55-7.63 (1H, m), 8.19 (1H, t), 8.79 (1H, t), 9.14 (1H, t);

Mass Spectrum: $C_{15}H_{11}FN_2O_2S$ requires 302; found 303 (MH$^+$).

Description 13

8-Amino-3-(4-chloro)phenylsulfonylquinoline (D13)

Prepared from 3-(4-chloro)phenylsulfonyl-8-nitro-quinoline (D21) in an analogous process to that described in Description 5 (D5);

$\delta_H$ (CDCl$_3$) 5.0 (2H, br s), 7.05 (1H, dd), 7.25 (1H, dd), 7.42-7.53 (3H, m), 7.95 (2H, dt), 8.68 (1H, d), 9.07 (1H, s);

Mass Spectrum: $C_{15}H_{11}N_2SO_2Cl$ requires 318, 320; found 319, 321 (MH$^+$).

Description 14

8-Amino-3-(3-fluoro)phenylsulfonylquinoline (D14)

Prepared from 3-(3-fluoro)phenylsulfonyl-8-nitro-quinoline (D22) in an analogous process to that described in Description 5 (D5);

$\delta_H$ (CDCl$_3$) 5.0 (2H, br s), 7.05 (1H, dd), 7.24-7.29 (2H, m), 7.44 (1H, d), 7.52 (1H, dt), 7.72 (1H, dt), 7.82 (1H, dt), 8.70 (1H, d), 9.09 (1H, d);

Mass Spectrum: $C_{15}H_{11}N_2O_2SF$ requires 302; found 303 (MH$^+$).

Description 15

8-Amino-3-(4-bromo-2-trifluoromethoxy)phenylsulfonylquinoline (D15)

Prepared from 3-(4-bromo-2-trifluoromethoxy)phenyl-8-nitro-sulfanylquinoline (D23) in an analogous process to that described in Description 5 (D5);

$\delta_H$ (CDCl$_3$) 5.0 (2H, br s), 7.07 (1H, dd), 7.26 (1H, dd), 7.43-7.48 (2H, m), 7.65 (1H, dd), 8.21 (1H, d), 8.72 (1H, d), 9.04 (1H, d);

Mass Spectrum: $C_{16}H_{10}N_2O_3SF_3Br$ requires 446, 448; found 447, 449 (MH$^+$).

Description 16

8-Amino-6-methyl-3-phenylsulfonylquinoline (D16)

Prepared from 6-methyl-8-nitro-3-phenylsulfonylquinoline (D24) in an analogous process to that described in Description 5 (D5);

$\delta_H$ (CDCl$_3$) 2.45 (3H, s), 4.94 (2H, br s), 6.90 (1H, s), 7.04 (1H, s), 7.50-7.60 (3H, m), 8.02 (2H, d), 8.60 (1H, s), 9.01 (1H, s);

Mass Spectrum: $C_{16}H_{14}N_2O_2S$ requires 298; found 299 (MH$^+$).

Description 17

8-Amino-3-(3-trifluoromethyl)phenylsulfonylquinoline (D17)

Prepared from 8-nitro-3-(3-trifluoromethyl)phenylsulfonylquinoline (D25) in an analogous process to that described in Description 5 (D5);

$\delta_H$ (CDCl$_3$) 5.0 (2H, br s), 7.06 (1H, dd), 7.27 (1H, d), 7.47 (1H, t), 7.69 (1H, t), 7.85 (1H, d), 8.20 (1H, d), 8.29 (1H, s), 8.73 (1H, d), 9.10 (1H, d);

Mass Spectrum: $C_{16}H_{11}N_2O_2SF_3$ requires 352; found 353 (MH$^+$).

Description 18

3-(2-Chloro)phenylsulfonyl-8-nitro-quinoline (D18)

A mixture of 3-(2-chloro)phenylsulfanyl-8-nitro-quinoline (D26) (0.63 g, 2.0 mmol) and 3-chloroperbenzoic acid (1.73 g, 10 mmol) in dichloromethane (10 ml) was stirred at room temperature for 3 h. The mixture was then diluted with dichloromethane (50 ml) and washed with saturated aqueous sodium metabisulfite (50 ml), saturated aqueous sodium hydrogencarbonate (50 ml), dried over magnesium sulfate and concentrated in vacuo to give the title compound (D18) (0.65 g, 94%) as an orange paste;

$\delta_H$ (CDCl$_3$) 7.06 (1H, d), 7.27 (1H, d), 7.44 (1H, s), 7.52-7.57 (3H, m), 8.48 (1H, d), 8.76 (1H, d), 9.05 (1H, d);

Mass Spectrum: $C_{15}H_9ClN_2O_4S$ requires 348, 350; found 349, 351 (MH$^+$).

Description 19

3-(3-Chloro)phenylsulfonyl-8-nitro-quinoline (D19)

Prepared from 3-(3-chloro)phenylsulfanyl-8-nitro-quinoline (D27) in an analogous process to that described in Description 18 (D18);

δ$_H$ (CDCl$_3$) 7.52 (1H, t), 7.62 (1H, d), 7.81 (1H, t), 7.93 (1H, d), 8.00 (1H, s), 8.21-8.24 (2H, m), 8.95 (1H, d), 9.39 (1H, d);

Mass Spectrum: C$_{15}$H$_9$ClN$_2$O$_4$S requires 348, 350; found 349, 351 (MH$^+$).

Description 20

3-(2-Fluoro)phenylsulfonyl-8-nitro-quinoline (D20)

Prepared from 3-(2-fluoro)phenylsulfanyl-8-nitro-quinoline (D28) in an analogous process to that described in Description 18 (D18);

δ$_H$ (CDCl$_3$) 7.17 (1H, t), 7.40 (2H, t), 7.65 (1H, m), 7.81 (1H, t), 8.20-8.27 (2H, m), 9.05 (1H, t), 9.40 (1H, t);

Mass Spectrum: C$_{15}$H$_9$FN$_2$O$_4$S requires 332; found 333 (MH$^+$).

Description 21

3-(4-Chloro)phenylsulfonyl-8-nitro-quinoline (D21)

Prepared from 3-(4-chloro)phenylsulfanyl-8-nitro-quinoline (D29) in an analogous process to that described in Description 18 (D18);

δ$_H$ (CDCl$_3$) 7.54 (2H, dt), 7.80 (1H, t), 7.97 (2H, dt), 8.20 (2H, d), 8.92 (1H, d), 9.37 (1H, d);

Mass Spectrum: C$_{15}$H$_9$N$_2$SO$_4$Cl requires 348, 350; found 349, 351 (MH$^+$).

Description 22

3-(3-Fluoro)phenylsulfonyl-8-nitro-quinoline (D22)

Prepared from 3-(3-fluoro)phenylsulfanyl-8-nitro-quinoline (D30) in an analogous process to that described in Description 18 (D18);

Mass Spectrum: C$_{15}$H$_9$N$_2$O$_4$SF requires 332; found 333 (MH$^+$).

Description 23

3-(4-Bromo-2-trifluoromethoxy)phenyl-8-nitro-sulfonylquinoline (D23)

Prepared from 3-(4-bromo-2-trifluoromethoxy)phenyl-8-nitro-sulfanylquinoline (D31) in an analogous process to that described in Description 18 (D18);

Mass Spectrum: C$_{16}$H$_8$N$_2$O$_5$SF$_3$Br requires 476, 478; found 479, 481 (MH$^+$).

Description 24

6-Methyl-8-nitro-3-phenylsulfonylquinoline (D24)

Prepared from 6-methyl-8-nitro-3-phenylsulfanylquinoline (D32) in an analogous process to that described in Description 18 (D18);

δ$_H$ (CDCl$_3$) 2.65 (3H, s), 7.60-7.67 (3H, m), 7.95 (1H, s), 8.00-8.05 (3H, m), 8.82 (1H, d), 9.30 (1H, d);

Mass Spectrum: C$_{16}$H$_{12}$N$_2$O$_4$S requires 328; found 329 (MH$^+$)

Description 25

8-Nitro-3-(3-trifluoromethyl)phenylsulfonylquinoline (D25)

Prepared from 8-nitro-3-(3-trifluoromethyl)phenylsulfanylquinoline (D33) in an analogous process to that described in Description 18 (D18);

δ$_H$ (CDCl$_3$) 7.75 (1H, t), 7.82 (1H, t), 7.91 (1H, d), 8.22-8.25 (3H, m), 8.30 (1H, s), 8.98 (1H, d), 9.40 (1H, d);

Mass Spectrum: C$_{16}$H$_9$N$_2$O$_2$SF$_3$ requires 381; found 382 (MH$^+$).

Description 26

3-(2-Chloro)phenylsulfanyl-8-nitro-quinoline (D26)

To a suspension of sodium hydride (0.16 g, 6.67 mmol) in dimethylformamide (10 ml) was slowly added 2-chlorothiophenol (0.96 g, 6.67 mmol) as a solution in dimethylformamide (5 ml). The reaction mixture was stirred for 10 minutes, then a solution of 3-iodo-8-nitroquinoline (D3) (1.0 g, 3.33 mmol) in dimethylformamide (5 ml) was added slowly and the mixture heated to 90° C. for 4 hours. The mixture was cooled to ambient temperature, then water (50 ml) was added carefully and the mixture extracted with dichloromethane (2×50 ml). The organic phase was washed with brine (50 ml), dried over magnesium sulfate and concentrated in vacuo. The crude material was purified by chromatography on silica, eluting with a hexane/ethyl acetate gradient to provide the title compound (D26) (0.70 g, 70%) as a brown oil;

δ$_H$ (CDCl$_3$) 7.25-7.28 (1H, m), 7.34 (1H, t), 7.40 (1H, d), 7.51 (1H, d), 7.63 (1H, t), 7.93 (1H, d), 8.02 (1H, d), 8.09 (1H, s), 8.87 (1H, s);

Mass Spectrum: C$_{15}$H$_9$ClN$_2$O$_2$S requires 316, 318; found 317, 319 (MH$^+$).

Description 27

3-(3-Chloro)phenylsulfanyl-8-nitro-quinoline (D27)

Prepared from 3-iodo-8-nitroquinoline (D3) and 3-chlorothiophenol in an analogous process to that described in Description 26 (D26);

δ$_H$ (CDCl$_3$) 7.35 (3H, br s), 7.45 (1H, s), 7.63 (1H, s), 7.92 (1H, s), 8.02 (1H, d), 8.10 (1H, s), 8.89 (1H, s);

Mass Spectrum: C$_{15}$H$_9$ClN$_2$O$_2$S requires 316, 318; found 317, 319 (MH$^+$).

Description 28

3-(2-Fluoro)phenylsulfanyl-8-nitro-quinoline (D28)

Prepared from 3-iodo-8-nitroquinoline (D3) and 2-fluorothiophenol in an analogous process to that described in Description 26 (D26);

δ$_H$ (CDCl$_3$) 7.21 (1H, d), 7.42-7.49 (2H, m), 7.53-7.62 (2H, m), 7.88 (1H, d), 7.97 (1H, d), 8.04 (1H, d), 8.86 (1H, d);

Mass Spectrum: $C_{15}H_9FN_2O_2S$ requires 300; found 301 (MH$^+$).

Description 29

3-(4-Chloro)phenylsulfanyl-8-nitro-quinoline (D29)

Prepared from 3-iodo-8-nitroquinoline (D3) and 4-chlorothiophenol in an analogous process to that described in Description 26 (D26);

$\delta_H$ (CDCl$_3$) 7.00 (1H, dd), 7.25-7.50 (3H, m), 7.56 (2H, d), 7.99 (1H, dd), 8.24 (1H, d), 8.81 (1H, d);

Mass Spectrum: $C_{15}H_9N_2O_2SCl$ requires 316, 318; found 317, 319 (MH$^+$)

Description 30

3-(3-Fluoro)phenylsulfanyl-8-nitro-quinoline (D30)

Prepared from 3-iodo-8-nitroquinoline (D3) and 3-fluorothiophenol in an analogous process to that described in Description 26 (D26);

$\delta_H$ (CDCl$_3$) 7.07 (1H, dt), 7.15 (1H, dt), 7.22 (1H, dt), 7.35 (1H, dd), 7.62 (1H, dd), 7.94 (1H, dd), 8.02 (1H, dd), 8.11, (1H, d), 8.89 (1H, d);

Mass Spectrum: $C_{15}H_9N_2SO_2F$ requires 300; found 301 (MH$^+$).

Description 31

3-(4-Bromo-2-trifluoromethoxy)phenyl-8-nitro-sulfanylquinoline (D31)

Prepared from 3-iodo-8-nitroquinoline (D3) and 4-bromo-2-trifluoromethoxythiophenol in an analogous process to that described in Description 26 (D26);

Mass Spectrum: $C_{16}H_8N_2O_3SF_3Br$ requires 444, 446; found 445, 447 (MH$^+$).

Description 32

6-Methyl-8-nitro-3-phenylsulfanylquinoline (D32)

Prepared from 3-bromo-6-methyl-8-nitroquinoline [for synthesis see Tinsley, *J. Am. Chem. Soc.*, 1955, 77, 4175] in an analogous process to that described in Description 26 (D26);

$\delta_H$ (CDCl$_3$) 2.56 (3H, s), 7.38-7.43 (3H, m), 7.47-7.51 (2H, m), 7.63 (1H, s), 7.82 (1H, s), 7.88 (1H, d), 8.78 (1H, d);

Mass Spectrum: $C_{16}H_{12}N_2O_2S$ requires 296; found 297 (MH$^+$).

Description 33

8-Nitro-3-(3-trifluoromethyl)phenylsulfanylquinoline (D33)

Prepared from 3-iodo-8-nitroquinoline (D3) and 3-trifluoromethylthiophenol in an analogous process to that described in Description 26 (D26);

$\delta_H$ (CDCl$_3$) 7.51 (1H, t), 7.59-7.67 (3H, m), 7.74 (1H, br s), 7.94 (1H, dd), 8.03 (1H, dd), 8.13 (1H, d), 8.90 (1H, d);

Mass Spectrum: $C_{16}H_9N_2SO_2F_3$ requires 350; found 351 (MH$^+$).

Description 34

8-Iodo-3-(3-trifluoromethyl)phenylsulfonylquinoline (D34)

Prepared from 8-amino-3-(3-trifluoromethyl)phenylsulfonylquinoline (D17) in an analogous process to that described in Description 6 (D6) in 44% yield;

$\delta_H$ (CDCl$_3$) 7.44 (1H, t), 7.71 (1H, t), 7.88 (1H, d), 8.00 (1H, dd), 8.22 (1H, d), 8.29 (1H, br s), 8.52 (1H, dd), 8.1 (1H, d), 9.33 (1H, d);

Mass Spectrum: $C_{16}H_9NO_2SIF_3$ requires 463; found 464 (MH$^+$).

General Procedure 1

The following intermediates were used to prepare Examples 18-20, 22-24, 29-31 and 34.

Description 4

Alternative Procedure

8-Nitro-3-phenylsulfonylquinoline (D4)

A 2 L vessel was charged with 3-Iodo-8-nitroquinoline (D3) (70.8 g, 236 mmol), copper (I) iodide (2.25 g, 11.8 mmol, 5 mol %), potassium phosphate (100 g, 472 mmol, 2 eq), ethylene glycol (0.71 L, 10 vol) and benzenethiol (36.2 ml, 354 mmol). The mixture was stirred and heated at 80° C. for 3.5 hours. The reaction mixture was cooled to 20° C. then H$_2$O (700 ml) and dichloromethane (700 ml) were added, the mixture was stirred for 5 minutes then the lower organic layer was removed (contained solids). Charcoal (35.4 g, Norit SX) was added to the organic layer and the mixture was stirred at room temperature for 15 min then filtered through GF/F filter paper. The filter cake was rinsed with dichloromethane (140 ml) and the combined filtrate was washed with H$_2$O (350 ml). The resulting dichloromethane solution was added to a suspension of magnesium monoperoxyphthalic acid hexahydrate (210 g, 424 mmol, 1.8 eq) in a mixture of dichloromethane (700 ml) and methanol (140 ml) over 45 minutes maintaining 18° C.<23° C. The resulting mixture was stirred rapidly for 2.25 hours at 20° C. to 23° C., then 10% w/v aqueous sodium sulfite (700 ml) was added over 15 minutes. the mixture was separated and treated with saturated aqueous sodium bicarbonate (280 ml). The mixture was stirred for 20 min before the layers were allowed to settle. The lower organic layer was removed, washed with water (280 ml), then concentrated at atmospheric pressure to ~210 ml. The resulting mixture was cooled to 0° C., stirred for 2 hrs then filtered. The filter cake was washed with cold (0-5° C.) dichloromethane (70 ml) then dried in vacuo at 25 to 40° C. to give the title compound (D4) as a light yellow solid in 64-66% yield, identical spectroscopically to that prepared by the earlier method.

Description 35

8-Amino-3-phenylsulfonylquinoline methanesulfonic acid salt (D35)

A suspension of iron powder (26.7 g, 5 eq, 325 mesh) in THF (300 ml, 10 vol), water (30 ml, 1 vol) and acetic acid (19.2 ml, 3.5 eq) was heated to 50° C. 8-Nitro-3-phenylsulfonylquinoline (D4) (30 g, 1 wt) was added portionwise to the mixture over 30 min, keeping the temperature below 60° C. The reaction mixture was stirred at 50 to 55° C. for 60 min. Toluene (240 ml, 8 vol) was added, followed by water (60 ml, 2 vol) before cooling to 40° C. and filtering the mixture through a silica gel plug. The silica plug was washed with toluene (2×60 ml, 2 vol). The layers of the combined filtrate were separated and the organic layer concentrated in vacuo to ca 10 volumes. The reaction mixture was warmed to 77° C. then treated with methanesulfonic acid (7.42 ml, 1.2 eq) added over 15 min maintaining the temperature at 75 to 80° C. The resulting orange suspension was cooled slowly to ambient, stirred at ambient temperature for ca 2 h, then the product filtered and washed with toluene (3×60 ml). The resulting pink solid (D35) was dried in vacuo at ca 45° C. to constant weight. Yield: 34.17 g, 94%.

$\delta_H$ (d6-DMSO) 2.46 (3H, s), 7.54 (1H, d, J=8 Hz), 7.60-7.70 (3H, m), 7.70-7.75 (1H, t, J=8 Hz), 7.81 (1H, J=8 Hz), 8.13 (2H, d, J=8 hz), 8.28 (3H, bs), 9.14 (1H, d, J=2 Hz), and 9.28 (1H, J=2 Hz).

Description 6

Alternative Procedure

8-Iodo-3-phenylsulfonylquinoline (D6)

A solution of sodium nitrite (5.44 g, 78.8 mmol, 1.2 eq) in water (125 ml, 5 vol) was added to a stirred slurry of 8-amino-3-phenylsulfonylquinoline methanesulfonic acid salt (D35) (25.0 g, 65.7 mmol) in 5M HCl (500 ml, 20 vol). The mixture was stirred at 23° to 24.5° C. for 1 hr 5 min then acetonitrile (200 ml, 8 vol) was added. After 10 min a solution of sodium iodide (14.8 g, 98.6 mmol, 1.5 eq) in water (125 ml, 5 vol) was added over 3 min, resulting in the formation of a brown mixture and the evolution of gas. The brown mixture was stirred at 25° C. to 23° C. for 1 hr 5 min then dichloromethane (500 ml, 20 vol) was added and the mixture was stirred for 5 min. The lower organic layer was removed and the aqueous layer was extracted with dichloromethane (125 ml, 5 vol). The combined organic layers were washed with 10% w/v sodium sulfite (125 ml, 5 vol) then concentrated under reduced pressure. The resulting mixture was filtered and the cake was washed with acetonitrile (2×25 ml) and dried in a 40° C. oven under reduced pressure to afford the title compound D6; yield 15.27 g, 59%, identical spectroscopically to that produced by the first method.

General Procedure 2

The following intermediates were used to prepare Examples 21, 25-28, 32 and 33.

Description 36

8-Nitro-3-(3-fluorophenyl)-sulfanylquinoline (D36)

A suspension of 3-iodo-8-nitroquinoline (D3) (4.5 g, 15 mmol), copper (I) iodide (150 mg, 0.8 mmol, 5 mol %), potassium phosphate (7.0 g, 2 eq), ethylene glycol (45 ml) and 3-fluorobenzenethiol (2.88 g, 22.5 mmol) was stirred and heated at 80° C. for 3.5 hours. The reaction mixture was cooled to 20° C. then $H_2O$ (45 ml) and dichloromethane (70 ml) were added, the mixture was stirred for 5 minutes then the lower organic layer was removed (contained solids). Charcoal (2 g, Norit SX) was added to the organic layer and the mixture was stirred at room temperature for 15 min then filtered The filter cake was rinsed with dichloromethane (40 ml) and the combined filtrate was washed with $H_2O$ (100 ml). The dichloromethane layer was evaporated to give the title compound as a yellow solid;

$\delta_H$ (CDCl$_3$): 7.07 (1H, dt), 7.15 (1H, dt), 7.24 (1H, t), 7.35 (1H, dd), 7.62 (1H, t), 7.92 (1H, d), 8.02 (1H, d), 8.11 (1H, d), 8.89 (1H, d);

Mass Spectrum: $C_{15}H_9N_2SO_2F$ requires 300; found 301 (MH$^+$).

Description 37

8-Amino-3-(3-fluoro)-phenylsulfanylquinoline (D37)

A suspension of iron powder (1.7 g, 30.4 mmol) in THF (20 ml), water (2 ml) and acetic acid (1.2 ml, 21 mmol) was heated to 50° C. 8-nitro-3-(3-fluorophenyl)-sulfanylquinoline (D36) (1.8 g, 6 mmol) was then added portionwise to the mixture over 15 minutes, keeping the temperature below 60° C. The reaction mixture was then stirred at 60° C. for 5 hours before the addition of toluene (5 ml). After allowing to cool to 60° C., the mixture was filtered through a silica plug, washing with toluene (2×20 ml). The volatiles were removed in vacuo and the residue purified by chromatography over silica gel, eluting with a gradient of ethyl acetate/hexane to afford the title compound as a solid (1.6 g, 5.7 mmol, 96%);

$\delta_H$ (CDCl$_3$): 5.0 (2H, br. s), 6.92-7.38 (7H, m), 8.12 (1H, d), 8.67 (1H, d);

Mass Spectrum: $C_{15}H_{11}N_2SF$ requires 270; found 271 (MH$^+$).

Description 38

8-Iodo-3-(3-fluoro)-phenylsulfanylquinoline (D38)

A solution of 8-amino-3-(3-fluoro)-phenylsulfanylquinoline (D37) (1.4 g, 5.2 mmol) in trifluoroacetic acid (5 ml) was concentrated in vacuo and the resulting oil dissolved in acetonitrile (10 ml). This was then added dropwise to an ice-cooled solution of n-butylnitrite (0.91 ml, 7.78 mmol) in acetonitrile (10 ml). The reaction mixture was then stirred at this temperature for 10 minutes followed by the portionwise addition of tetra-n-butylammonium iodide (3.8 g, 10.4 mmol). After allowing to stir at ambient temperature for 1 hour, the mixture was concentrated in vacuo and the residue purified by chromatography over silica gel, eluting with a gradient of ethyl acetate/hexane to afford the title compound (D38) as a solid (1.13 g, 3.0 mmol, 57%);

Mass Spectrum: $C_{15}H_9NSFI$ requires 281; found 282 (MH$^+$).

Description 39

8-Iodo-3-(3-fluoro)-phenylsulfonylquinoline (D39)

A solution of 8-Iodo-3-(3-fluoro)-phenylsulfanylquinoline (D38) (754 mg 2.0 mmol) in dichloromethane (10 ml) was treated with a solution of monomagnesium peroxyphthalate hexahydrate (2 g, technical) in methanol (3 ml). The mixture was warmed to 40° C. for 12 hours, then treated with 10% aqueous sodium sulfite (20 ml) and dichloromethane (20 ml). The organic phase was separated and washed successively with sat. aq. sodium bicarbonate solution (20 ml) and brine (5 ml), before being concentrated and the residue purified by flash chromatography on silica gel (eluting with hexane-dichloromethane) to afford the title compound (D39) as a pale yellow solid in 50% yield;

δ$_H$ (CDCl$_3$): 7.30 (1H, dt), 7.41 (1H, t), 7.53 (1H, dt), 7.73 (1H, dt), 7.83 (1H, d), 7.97 (1H, d), 8.52 (1H, d), 8.78, (1H, d), 9.32 (1H, d);

Mass Spectrum: C$_{15}$H$_9$NO$_2$SFI requires 313; found 314 (MH$^+$).

Example 1

8-(4-Methyl-piperazin-1-yl)-3-phenylsulfonylquinoline (E1)

A 4:1 mixture of 3-iodo-8-(4-methyl-piperazin-1-yl)-quinoline (D2) and 3-bromo-8-(4-methyl-piperazin-1-yl)-quinoline (D1) (1.5 g), phenylsulfonic acid sodium salt, dihydrate (2.52 g, 12.6 mmol) and copper (I) iodide (2.4 g, 12.6 mmol) in N,N-dimethylformamide (25 ml) was stirred in an oil bath at 120° C. for 40 h under argon. To the reaction mixture, cooled to ambient temperature, was added 5% sodium hydrogen carbonate solution (100 ml) and dichloromethane (100 ml) with vigorous shaking. The insoluble material was filtered, washed with dichloromethane (3×20 ml) and discarded. The filtrate and washings were transferred to a separating funnel and the layers separated. The aqueous layer was extracted with dichloromethane (100 ml) and the combined organic extracts were washed with water (100 ml), dried (MgSO$_4$) and concentrated in vacuo to an oil (0.9 g). The oil was purified by chromatography over silica gel eluting with a gradient of methanol/dichloromethane to afford an orange oil (0.28 g, Rf 0.11, methanol/dichloromethane 1:19). This material was further purified by passage through a strong cation exchange (SCX) column eluting firstly with methanol (fractions discarded) and then with methanol/aqueous ammonia-880 (10:1) to give the title compound (E1) as an orange oil (0.152 g, 0.41 mmol, 7% over two steps);

δ$_H$ (CDCl$_3$) 2.40 (3H, s), 2.72-2.76 (4H, m), 3.44 (4H, br s), 7.25-7.27 (1H, m), 7.48-7.61 (5H, m), 7.99-8.02 (2H, m), 8.75 (1H, d, J=2.4 Hz), 9.21 (1H, d, J=2.4 Hz);

Mass Spectrum: C$_{20}$H$_{21}$N$_3$O$_2$S requires 367; found 368 (MH$^+$).

Example 1

Alternative Procedure

8-(4-Methyl-piperazin-1-yl)-3-phenylsulfonylquinoline (E1)

A solution of 8-amino-3-phenylsulfonylquinoline (D5) (38.8 g, 137 mmol) in n-butanol (360 ml) was treated with bis-(2-chloroethyl)-methyl-amine hydrochloride (40 g, 138 mmol) and sodium carbonate (72 g, 0.68 mol). The mixture was heated to a vigorous reflux (~100° C.) for 16 h then a further portion of bis-(2-chloroethyl)-methyl-amine hydrochloride (25 g, 86 mmol) introduced and heating continued for a further 4 h. The solution was cooled and a 1:1 mixture of saturated aqueous sodium bicarbonate and aqueous 10% sodium thiosulphate solution (2 L) added. Stirring was continued at ambient temperature for 16 h then the aqueous phase was extracted with dichloromethane (3×500 ml), the combined organic phase dried over magnesium sulphate, evaporated in vacuo and subjected to chromatography on a Biotage Flash 75 apparatus (1 kg Silica gel) to afford the title compound (E1) as the free base form (11.6 g), identical spectroscopically to that prepared by the first method.

A portion of this material was treated with 1M HCl in ether then evaporated to afford the hydrochloride salt as a yellow solid;

δ$_H$ (CDCl$_3$) 2.95 (3H, d), 2.38-3.52 (4H, m), 4.01-4.06 (2H, m), 4.19-4.26 (2H, m), 7.60 (2H, t), 7.70 (1H, t), 7.96 (1H, t), 8.07 (2H, s), 8.09 (2H, s), 9.34 (1H, d), 9.63 (1H, d), 12.9 (1H, br s)

Example 1

Alternative Procedure

8-(4-Methyl-piperazin-1-yl)-3-phenylsulfonylquinoline (E1)

8-Iodo-3-phenylsulfonyl-quinoline (D6) (190 mg, 0.48 mmol), N-methyl-piperazine (48 mg, 0.48 mmol), sodium tertbutoxide (65 mg, 0.68 mmol), di-palladium tetrakis-(dibenzylidine acetone) [Pd$_2$(dba)$_3$] (88 mg, 0.1 mmol) and 1,1'-diphenylphosphino ferrocene (161 mg, 0.3 mmol) were suspended in degassed dry dioxan (2 ml). The mixture was stirred under argon at 40° C. for 16 hours. The solvent was removed and the residue subjected to flash chromatography on silica gel (eluting with dichloromethane-methanol aq. ammonia) to give the title compound (E1), identical spectroscopically to that prepared by the earlier methods.

Example 2

3-Phenylsulfonyl-8-piperazin-1-yl-quinoline hydrochloride (E2)

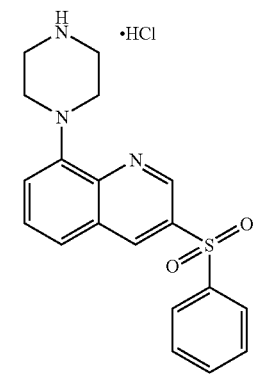

A stirred solution of 8-(4-methyl-piperazin-1-yl)-3-phenylsulfonylquinoline (E1) (0.148 g, 0.4 mmol), 1-chloroethyl chloroformate (0.093 ml, 0.85 mmol) and N,N-diisopropylethylamine (0.148 ml, 0.85 mmol) in 1,2-dichloroethane (9 ml) was heated at reflux for 1.25 h under argon. The reaction mixture was cooled to ambient temperature and concentrated in vacuo to an oil. The oil was purified by chromatography over silica gel eluting with a gradient of methanol/dichloromethane, pooling fractions which contained the major component (Rf 0.9, methanol/dichloromethane 1:19). The purified material was redissolved in methanol (15 ml) and the solution was refluxed for 1 h under argon. The reaction mixture was cooled to ambient temperature and concentrated in vacuo to a solid which was stirred with diethyl ether (5 ml) and filtered to afford the title compound (E2) (0.08 g, 0.21 mmol, 51%);

δ$_H$ (d$_6$-DMSO) 3.32 (4H, br s), 3.55 (4H, br s), 7.35 (1H, d, J=6.5 Hz), 7.63-7.77 (4H, m), 7.86 (1H, d, J=7.4 Hz), 8.10 (2H, m), 9.10 (1H, d, J=2.4 Hz), 9.21 (2H, s), 9.24 (1H, d, J=2.4 Hz);

Mass Spectrum: $C_{19}H_{19}N_3O_2S$ requires 353; found 354 (MH$^+$).

Example 2

Alternative Procedure

3-Phenylsulfonyl-8-piperazin-1-yl-quinoline hydrochloride (E2)

A mixture of 8-(4-t-butoxycarbonyl)piperazin-1-yl-3-phenylsulfonylquinoline (D7), 1,4-dioxane and 4 M aqueous HCl, was stirred at ambient temperature for two hours, then the solvent evaporated. The residue was co-evaporated several times from toluene and the remainder crystallised from hot ethanol to give the title compound (E2) as a yellow crystalline solid;

$\delta_H$ (d$_6$-DMSO) 3.32 (4H, br s), 3.55 (4H, br s), 7.35 (1H, d, J=6.5 Hz), 7.63-7.77 (4H, m), 7.86 (1H, d, J=7.4 Hz), 8.10 (2H, m), 9.10 (1H, d, J=2.4 Hz), 9.21 (2H, s), 9.24 (1H, d, J=2.4 Hz);

Mass Spectrum: $C_{19}H_{19}N_3O_2S$ requires 353; found 354 (MH$^+$);

m.p. 200° C. (phase change), 270-274° C. (decomposed)

Example 3

3-(2-Chloro)phenylsulfonyl-8-piperazin-1-yl-quinoline hydrochloride (E3)

bis-(2-Chloro-ethyl)-amine hydrochloride (0.36 g, 1.89 mmol) and sodium carbonate (0.50 g, 4.72 mmol) were added to a suspension of 8-amino-3-(2-chloro)phenylsulfonylquinoline (D10) (0.30 g, 0.94 mmol), in n-butanol (10 ml). The stirred suspension was heated at reflux for 48 h. The reaction mixture was cooled to ambient temperature, diluted with dichloromethane (50 ml) and the solution washed with water (50 ml), dried (MgSO$_4$) and concentrated in vacuo to an oil. The oil was purified by chromatography over silica gel eluting with a gradient of methanol/dichloromethane to afford 3-(2-chlorophenylsulfonyl)-8-(4-methylpiperazin-1-yl)quinoline as an oil (0.17 g, 44%). A stirred solution of 3-(2-chlorophenylsulfonyl)-8-(4-methylpiperazin-1-yl) quinoline (0.17 g, 0.42 mmol), 1-chloroethyl chloroformate (0.14 ml, 1.27 mmol) and N,N-diisopropylethylamine (0.22 ml, 1.27 mmol) in 1,2-dichloroethane (8 ml) was heated at reflux for 1 h under argon. The reaction mixture was cooled to ambient temperature and concentrated in vacuo to an oil. This material was redissolved in methanol (10 ml) and the solution was refluxed for 1 h under argon. The reaction mixture was cooled to ambient temperature and concentrated in vacuo to a solid which was purified by preparative HPLC. The pure material was stirred with 1 M HCl/diethyl ether (5 ml) and methanol (5 ml), then the resulting mixture was evaporated in vacuo to afford the title compound (E3);

$\delta_H$ (CD$_3$OD) 3.31 (4H, br s), 3.53 (4H, br s), 7.57 (1H, d), 7.61 (1H, d), 7.69 (2H, t), 7.75 (1H, t), 7.89 (1H, d), 8.48 (1H, d), 9.10 (1H, s), 9.25 (1H, s);

Mass Spectrum: $C_{19}H_{18}ClN_3O_2S$ requires 387; found 388 (MH$^+$).

Example 4

3-(3-Chloro)phenylsulfonyl-8-piperazin-1-yl-quinoline hydrochloride (E4)

Prepared from 8-amino-3-(3-chloro)phenylsulfonylquinoline (D11) in an analogous process to that described in Example 3 (E3);

$\delta_H$ (CD$_3$OD) 3.31 (4H, br s), 3.53 (4H, br s), 7.56-7.64 (2H, m), 7.69-7.76 (2H, m), 7.87 (1H, d), 8.01 (1H, d), 8.13 (1H, s), 9.12 (1H, s), 9.29 (1H, s);

Mass Spectrum: $C_{19}H_{18}ClN_3O_2S$ requires 387, 389; found 388, 390 (MH$^+$).

Example 5

3-(2-Fluoro)phenylsulfonyl-8-piperazin-1-yl-quinoline hydrochloride (E5)

Prepared from 8-amino-3-(2-fluoro)phenylsulfonylquinoline (D12) in an analogous process to that described in Example 3 (E3);

$\delta_H$ (CD$_3$OD) 3.51 (4H, br s), 3.59 (4H, br s), 7.30 (1H, t), 7.49 (1H, t), 7.54 (1H, d), 7.72 (2H, t), 7.86 (1H, d), 8.23 (1H, t), 9.05 (1H, s), 9.27 (1H, br s);

Mass Spectrum: $C_{19}H_{18}FN_3O_2S$ requires 371; found 372 (MH$^+$).

Example 6

3-(4-Chloro)phenylsulfonyl-8-piperazin-1-yl-quinoline hydrochloride (E6)

Prepared from 8-amino-3-(4-chloro)phenylsulfonylquinoline (D13) in an analogous process to that described in Example 3 (E3);

$\delta_H$ (CD$_3$OD) 3.54-3.57 (8H, br s), 7.63 (2H, d), 7.84 (2H, br s), 8.03-8.06 (1H, m), 8.12 (2H, d), 9.39 (2H, br s);

Mass Spectrum: $C_{19}H_{18}ClN_3O_2S$ requires 387; found 388 (MH$^+$).

Example 7

3-(3-Fluoro)phenylsulfonyl-8-piperazin-1-yl-quinoline hydrochloride (E7)

Prepared from 8-amino-3-(3-fluoro)phenylsulfonylquinoline (D14) in an analogous process to that described in Example 3 (E3);

$\delta_H$ (CD$_3$OD) 3.53-3.68 (8H, m), 7.41-7.56 (2H, m), 7.62-7.75 (2H, m), 7.85-7.95 (3H, m), 9.09 (1H, d), 9.27 (1H, d);

Mass Spectrum: $C_{19}H_{18}FN_3O_2S$ requires 371; found 372 (MH$^+$).

Example 8

3-(4-Bromo-2-trifluoromethoxy)phenylsulfonyl-8-piperazin-1-yl-quinoline hydrochloride (E8)

Prepared from 8-amino-3-(4-bromo-2-trifluoromethoxy) phenylsulfonylquinoline (D15) in an analogous process to that described in Example 3 (E3);

$\delta_H$ (CD$_3$OD) 3.54 (4H, m), 3.60 (4H, m), 7.58 (1H, dd), 7.66 (1H, t), 7.74 (1H, t), 7.86 (2H, dd), 8.30 (1H, d), 9.03 (1H, d), 9.23 (1H, d);

Mass Spectrum: $C_{20}H_{17}BrF_3N_3O_3S$ requires 515, 517; found 516, 518 (MH$^+$).

Example 9

8-Piperazin-1-yl-3-(3-trifluoromethyl)phenylsulfonylquinoline hydrochloride (E9)

To a stirred solution of 8-(4-t-butyloxycarbonyl)piperazin-1-yl-3-(3-trifluoromethyl)phenylsulfonylquinoline (D8)

(0.33 g, 0.63 mmol) in dioxane (10 ml) was added 4 M HCl (10 ml). After stirring for 4 h, the solvents were removed in vacuo to afford the title compound (E9) as a colourless solid (0.30 g, 97%);

$\delta_H$ (CD$_3$OD) 3.54-3.63 (8H, m), 7.88-8.00 (3H, m), 8.03-15 (2H, m), 8.44 (2H, d), 9.48 (1H, d), 9.56 (1H, d);

Mass Spectrum: C$_{20}$H$_{18}$F$_3$N$_3$O$_2$S requires 421; found 422 (MH$^+$).

Example 10

7-Chloro-3-phenylsulfonyl-8-piperazin-1-yl-quinoline hydrochloride (E10)

To a stirred solution of 3-phenylsulfonyl-8-piperazin-1-yl-quinoline hydrochloride (E2) (54 mg, 0.14 mmol) in glacial acetic acid (0.5 ml), at room temperature was added N-chlorosuccinimide (19 mg, 0.14 mmol). After 16 h the solvent was removed and the mono chlorinated product isolated by preparative reverse phase gradient chromatography (10-90% acetonitrile in water). After removal of the solvents the residue was dissolved in methanol and treated with a solution of hydrogen chloride in diethyl ether (1 M). The solvent was removed to afford the title compound (E10) (9 mg 17%);

$\delta_H$ (CDCl$_3$) 3.4 (4H, br.m), 3.6 (4H, v.br m), 7.61 (3H, m), 7.68 (2H, t), 8.05 (2H, d), 8.77 (1H, d), 9.22 (1H, d), 9.74 (2H, br NH$_2$);

Mass Spectrum: C$_{19}$H$_{18}$ClN$_3$O$_2$S requires 387, 389; found 388, 390 (ES+) (MH$^+$).

Example 11

6-Methyl-3-phenylsulfonyl-8-piperazin-1-yl-quinoline hydrochloride (E11)

Prepared from 8-amino-6-methyl-3-phenylsulfonylquinoline (D16) using an analogous process to that described in Example 3 (E3);

$\delta_H$ (CD$_3$OD) 2.51 (3H, s), 3.30 (4H, br s), 3.55 (41-1, br s), 7.32 (1H, s), 7.26-7.67 (4H, m), 8.07 (2H, d), 8.88 (1H, d), 9.14 (1H, d);

Mass Spectrum: C$_{20}$H$_{21}$N$_3$O$_2$S requires 367; found 368 (MH$^+$).

Example 12

(R)-8-(3-Methyl)piperazin-1-yl-3-phenylsulfonylquinoline hydrochloride (E12)

8-Iodo-3-phenylsulfonylquinoline (D6) (200 mg, 0.51 mmol) was dissolved in dry, de-gassed dioxane (4 ml) under argon. To this solution was added sodium t-butoxide (68 mg, 0.71 mmol) and (R)-(−)-2-methylpiperazine (61 mg, 0.61 mmol) followed by a suspension of catalyst under argon. The catalyst was prepared by sonicating tris-(dibenzylideneacetone)dipalladium(0) (14 mg, 0.015 mmol) and 2-dicyclohexylphosphino-2'-(N,N-dimethylamino)biphenyl (18 mg, 0.015 mmol) in dry degassed dioxane (1 ml) for 2 minutes. This mixture was stirred at 40° C. for 5 h then a further charge of catalyst was administered (prepared as above on half the scale) and stirring continued for 16 h at 40° C.

The mixture was filtered and the solvent removed. The residue was dissolved in methanol and passed down an SCX ion exchange column eluting with methanol to remove impurities. The product was recovered by eluting with 15% 0.880 aqueous ammonia in methanol. The solvent was removed and the residue dissolved in methanol and treated with a solution of hydrogen chloride in diethyl ether (1 M). The solvent was removed and the residue recrystallised from ethanol to afford the title compound (E12) (40 mg 16%);

$\delta_H$ (CD$_3$OD): 1.40 (3H, d), 2.96 (1H, t), 3.19 (1H, m), 3.51 (2H, m), 3.69 (1H, m), 3.95 (2H, d), 7.46 (1H, d), 7.62-7.70 (4H, m), 7.81 (1H, d), 8.09 (2H, d), 8.99 (1H, d), 9.22 (1H, d);

Mass Spectrum: C$_{20}$H$_{21}$N$_3$O$_2$S requires 367; found 368 (MH$^+$).

Example 13

(S)-8-(3-Methyl)piperazin-1-yl-3-phenylsulfonylquinoline hydrochloride (E13)

Prepared from (S)-(+)-2-methylpiperazine in place of (R)-(−)-2-methylpiperazine using an analogous process to that described in Example 12 (E12) affording the title compound (E13) (77 mg, 37%) as a yellow solid;

$\delta_H$ (CD$_3$OD): 1.40 (3H, d), 2.96 (1H, t), 3.19 (1H, m), 3.51 (2H, m), 3.69 (1H, m), 3.95 (2H, d), 7.46 (1H, d), 7.62-7.70 (4H, m), 7.81 (1H, d), 8.09 (2H, d), 8.99 (1H, d), 9.22 (1H, d);

d (62.9 MHz, CD$_3$OD) C 16.7 (CH$_3$), 45.1 (CH$_2$), 48.4 (CH$_2$), 53.3 (CH), 56.8 (CH$_2$), 122.5 (CH), 125.8 (CH), 129.4 (2×HC), 130.0 (C), 130.6 (CH), 131.3 (2×CH), 135.6 (CH), 137.0 (C), 140 (CH), 142.7 (C), 144.5 (C), 146.4 (CH), 149.0 (C). Mass Spectrum: C$_{20}$H$_{21}$N$_3$O$_2$S requires 367; found 368 (MH$^+$).

mp 266-269° C. with decomp. (crystallised from IPA).

Example 14

8-Homopiperazin-1-yl-3-phenylsulfonylquinoline hydrochloride (E14)

Crude 8-(4-t-butoxycarbonyl)homopiperazin-1-yl-3-phenylsulfonylquinoline (D9) was suspended in a mixture of dioxane (2 ml) and 4 M hydrochloric acid (2 ml) and stirred at 80° C. for 1 h to form a homogeneous solution. The solvents were removed and the residue dissolved in methanol and passed down an SCX ion exchange column eluting with methanol. The product was recovered by further elution with 15% 0.880 aqueous ammonia in methanol. The solvents were removed and residue treated with a solution of hydrogen chloride in diethyl ether (1M). The solvents were removed and the residue recrystallised from ethanol to afford the title compound (E14) (20 mg, 10%);

$\delta_H$ (CD$_3$OD): 2.31 (2H, m), 3.45 (2H, m), 3.55 (2H, m), 3.74 (4H, m), 7.40 (1H, d), 7.60-7.70 (5H, m), 8.08 (2H, m), 8.94 (1H, d), 9.18 (1H, d);

Mass Spectrum: C$_{20}$H$_{21}$N$_3$O$_2$S requires 367; found 368 (MH$^+$).

Example 15

8-((S)-2-Methyl-piperazin-1-yl)-3-phenylsulfonylquinoline hydrochloride (E15)

(S)-3-Methyl-4-(3-phenylsulfonyl-quinolin-8-yl)-piperazine-1-carboxylic acid tert-butyl ester was prepared in accordance with the procedure described in Description 7 (D7) by replacing piperazine-1-carboxylic acid tert-butyl ester with (S)-3-methyl-piperazine-1-carboxylic acid tert-butyl ester. This material was then treated to the conditions described in Example 2 (Alternative Procedure) to afford the title compound (E15);

$\delta_H$ (CD$_3$OD): 0.92 (3H, d), 3.25 (1H, m), 3.43 (3H, m), 3.57 (2H, m), 4.09 (1H, br s), 7.64 (2H, t), 7.71 (1H, t), 7.90 (1H, t), 7.98 (1H, d), 8.14 (3H, m), 9.38 (1H, s), 9.39 (1H, s);

Mass spectrum: C$_{20}$H$_{21}$N$_3$O$_2$S requires 367; found 368 (MH$^+$).

Example 16

3-Phenylsulfonyl-8-piperazin-1-yl-quinoline (E16), (free base form of E2)

A 100 ml three necked flask was charged with Pd$_2$(dba)$_3$ (174 mg, 0.19 mmol, 0.03 eq), 8-Iodo-3-phenylsulfonylquinoline (D6) (2.5 g, 6.33 mmol), 1,1'-bis-diphenylphosphenoferrocene (316 mg, 0.57 mmol), sodium tertbutoxide (851 mg, 8.86 mmol, 1.4 eq) and piperazine (2.72 g, 31.6 mmol, 5 eq). The flask was evacuated and filled with nitrogen 4 times then anhydrous 1,4-dioxane (17.5 ml, 7 vol) was added. The mixture was stirred and heated to 40° C. for 16½ hrs.

The dark solution was allowed to cool to room temperature, dichloromethane (12.5 ml) was added and the solution was washed with H$_2$O (12.5 ml). The aqueous wash was extracted with dichloromethane and the combined organic layers were extracted with 5M HCl (2×12.5 ml). The combined aqueous layers were washed with (dichloromethane 2.5 ml) then transferred to a conical flask, dichloromethane (12.5 ml) was added and the flask was cooled in an ice/water bath. 10M Aqueous sodium hydroxide (13 ml) was added whilst stirring, the mixture was then stirred at room temperature until all the solids were dissolved. The lower organic layer was removed and the aqueous layer was extracted with dichloromethane (7.5 ml), the combined organic layers were concentrated under reduce pressure to ~5 ml. Isooctane (2.5 ml) was added to the dark brown solution resulting in crystallisation, the mixture was stirred at room temp for 5 min then isooctane (22.5 ml) was added over 5 min. The mixture was aged at room temp for 1½ hrs before being cooled in an ice/water bath for 30 min, the mixture was filtered and the cake washed with isooctane (5 ml). The cake was dried under reduced pressure to give the title compound E16; yield 1.67 g, 75%.

$\delta_H$ (CDCl$_3$): 1.6 (1H, bs), 3.18 (4H, m), 3.34 (4H, m), 7.27 (1H, m), 7.49-7.60 (5H, m), 8.01 (2H, dd), 8.75, (1H, d), 9.21 (1H, d).

Example 17

8-(4-Ethyl-piperazin-1-yl)-3-phenylsulfonylquinoline hydrochloride (E17)

A suspension of 3-phenylsulfonyl-8-piperazin-1-yl-quinoline (E16) (200 mg, 0.55 mmol) in ethanol (4 ml) was treated successively with acetic acid (100 μl), acetylaldehyde (100 mg, 2.3 mmol) and resin bound Amberlyst cyanoborohydride (~3 mmol/g, 0.5 g). The mixture was stirred at ambient temperature for 18 hours then filtered and the filtrate absorbed onto an SCX cartridge. This was washed with ethanol then eluted with a solution of 3% ammonia in 7% aqueous methanol. The solution was evaporated and the residue subjected to purification by flash chromatography on silica gel (eluting with dichloromethane-methanol-aq. NH$_3$) to give a solution of the free base of the title compound. this was evaporated and treated with 1M HCl in ether then crystallised from isopropanol to give the title compound (E17) as a yellow solid.

$\delta_H$ (CDCl$_3$): 1.54 (3H, t), 3.22 (2H, q), 3.27-3.91 (8H, m), 7.23-7.70 (m, 6H), 8.03 (2H, d), 8.80 (1H, s), 9.22 (1H, s), 12.5 (1H, br.s);

Mass Spectrum: C$_{17}$H$_{23}$N$_3$O$_2$S requires 381; found 382 (MH$^+$).

Examples 18-21

E18-21

Examples 18-21 were prepared using the method described for Example 16 from the appropriate substituted 3-arylsulfonyl-8-iodoquinoline (derived from the appropriate thiol, tabulated below, using General Procedures 1 or 2) in place of 3-phenylsulfonyl-8-iodoquinoline (D6).

| Example | Q$^1$ | General Procedure | Starting Thiol | M + H$^+$ |
| --- | --- | --- | --- | --- |
| 18 | 2-Me | 1 | 2-Methyl-benzenethiol | 368 |
| 19 | 2-OMe | 1 | 2-Methoxy-benzenethiol | 384 |
| 20 | 4-Me | 1 | 4-Methyl-benzenethiol | 368 |
| 21 | 4-F | 2 | 4-Fluoro-benzenethiol | 372 |

Examples 22-28

E22-28

Examples 22-28 were prepared using the method described for Example 1 (Alternative Procedure 3) from the appropriate substituted 3-arylsulfonyl-8-iodoquinoline (derived from the appropriate thiol, tabulated below, using General Procedures 1 or 2) in place of 3-phenylsulfonyl-8-iodoquinoline (D6).

| Example | Q$^1$ | General Procedure | Starting Thiol | M + H$^+$ |
| --- | --- | --- | --- | --- |
| 22 | 2-Me | 1 | 2-Methyl-benzenethiol | 382 |
| 23 | 2-OMe | 1 | 2-Methoxy-benzenethiol | 398 |

-continued

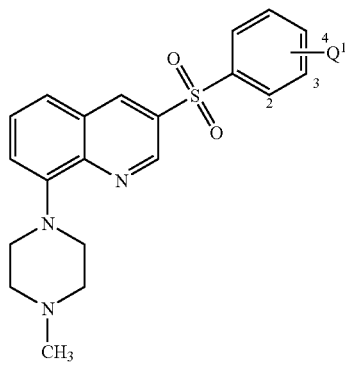

| Example | Q¹ | General Procedure | Starting Thiol | M + H⁺ |
|---|---|---|---|---|
| 24 | 4-Me | 1 | 4-Methyl-benzenethiol | 382 |
| 25 | 4-F | 2 | 4-Fluoro-benzenethiol | 386 |
| 26 | 3-F | 2 | 3-Fluoro-benzenethiol | 386 |
| 27 | 2-F | 2 | 2-Fluoro-benzenethiol | 386 |
| 28 | 4-Cl | 2 | 4-Chloro-benzenethiol | 402, 404 |

Examples 29-34

E29-34

Examples 29-34 were prepared using the method described for Example 13, using the appropriate substituted 3-arylsulfonyl-8-iodoquinoline (derived from the appropriate thiol, tabulated below, using General Procedures 1 or 2) in place of 3-phenylsulfonyl-8-iodoquinoline (D6).

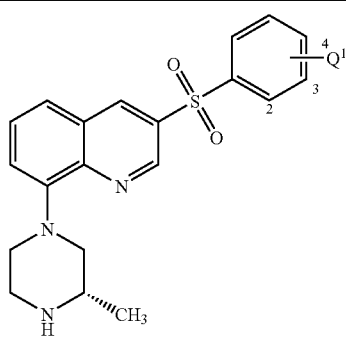

| Example | Q¹ | General Procedure | Starting Thiol | M + H⁺ |
|---|---|---|---|---|
| 29 | 2-Me | 1 | 2-Methyl-benzenethiol | 382 |
| 30 | 2-OMe | 1 | 2-Methoxy-benzenethiol | 398 |
| 31 | 4-Me | 1 | 4-Methyl-benzenethiol | 382 |
| 32 | 4-F | 2 | 4-Fluoro-benzenethiol | 386 |
| 33 | 3-F | 2 | 3-Fluoro-benzenethiol | 386 |
| 34 | 3-Cl | 1 | 3-Chloro-benzenethiol | 402, 404 |

Examples 35-37

E35-37

Examples 35-37 were prepared using the methods described for Example 16 or 15 using the tabulated amines in place of piperazine or 2-(S)-methylpiperazine, respectively.

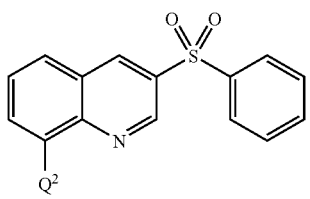

| Example | Q² | Analogous Procedure | Amine | M + H⁺ |
|---|---|---|---|---|
| 35 | 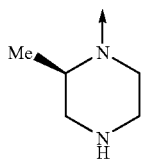 | Example 15 | 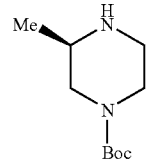 | 368 |
| 36 | 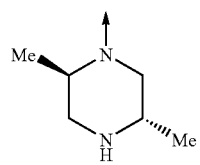 | Example 16 | | 382 |

-continued

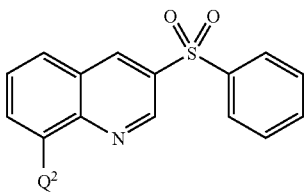

| Example | Q² | Analogous Procedure | Amine | M + H⁺ |
|---|---|---|---|---|
| 37 | (piperazine-pyrrolidine bicyclic N-linked) | Example 16 | (octahydropyrrolo[1,2-a]pyrazine) | 394 |

Examples 38-42

E38-42

Examples 38-42 were prepared using the method described for Example 17 utilising the amines tabulated below, and carbonyl compounds tabulated below in place of acetaldehyde.

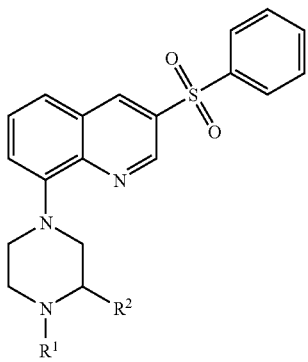

| Example | R¹ | R² | Amine | aldehyde/ketone | M + H⁺ |
|---|---|---|---|---|---|
| 38 | iPr | H | E2 | acetone | 396 |
| 39 | iBu | H | E2 | isobutyraldehyde | 410 |
| 40 | 2,2-dimethyl-propyl | H | E2 | 2,2-dimethylpropionaldehyde | 424 |
| 41 | Me | (R)—Me | E12 | 37% formaldehyde in aq. Methanol | 382 |
| 42 | Me | (S)—Me | E13 | 37% formaldehyde in aq. Metahnol | 382 |

Example 43

3-Phenylsulfonyl 8-({1S,4S}2,5-diazabicycloheptan-2-yl) quinoline hydrochloride (E43)

3-sulfonyl-8-iodo quinoline (D6) (200 mg, 0.48 mMol), (1S,4S)-2,5-diaza-bicyclo[2.2.1]heptane-2-carboxylic acid tert-butyl ester (95 mg, 0.48 mmol), sodium ᵗbutoxide (65 mg, 0.68 mmol), di-palladium tetrakis-(dibenzylidene acetone) (88 mg, 0.1 mmol) and 1,1'-diphenylphosphino ferrocene (161 mg, 0.3 mMol) were suspended in degassed dry dioxan (2 ml). The mixture was stirred under argon at 40° C. for 16 hours. The solvent was removed and the residue was purified by chromatography on silica using 30% ethyl acetate in hexane to afford (1S,4S)-5-(3-benzenesulfonyl-quinolin-8-yl)-2, 5-diaza-bicyclo[2.2.1]heptane-2-carboxylic acid tert-butyl ester in 70% yield. This material (160 mg) was treated with 4M hydrochloric acid (1 ml) and dioxan (1 ml) with stirring at 80° C. for 30 mins. The solvent was removed to afford the title compound (E43) as a yellow solid;

δH MeOD-d₄) 1.96 (1H, d), 2.16 (1H, d), 3.37 (2H, m), 3.69 (1H, m), 4.17 (1H, m), 4.41 (1H, s), 5.17 (1H, s), 7.06 (1H, dd) 7.53-7.98 (4H, m), 8.08 (1H, m), 8.88 (1H, d), 9.08 (1H, d), 9.00 (1H, d), 9.55 (1H, br, s);

Found [M+1]⁺ 366 ($C_{20}H_{19}N_3O_2S$).

Example 44

Crystallisation of 3-phenylsulfonyl-8-piperazin-1-yl-quinoline (Form I)

3-Phenylsulfonyl-8-piperazin-1-yl-quinoline (E16) (0.1 g) was dissolved in ethyl acetate (1.7 ml) with warming. On cooling the product crystallised as needles. Solvent was allowed to evaporate to afford the title compound in quantitative recovery. Melting point 158° C.

Characterising data recorded for Form I:

The infrared spectrum of the solid product was recorded using a Nicolet Avatar 360 FT-IR spectrometer fitted with a universal ATR accessory. The FT-IR spectrum (FIG. 1) shows bands at: 2945, 2819, 1606, 1590, 1566, 1487, 1469, 1447, 1380, 1323, 1283, 1247, 1164, 1138, 1126, 1107, 1095, 1083, 1056, 1026, 997, 964, 949, 919, 906, 879, 859, 824, 785, 761, 723, 705 cm$^{-1}$ The FT-Raman spectrum was acquired using a ThermNicolet 960 E.S.P. spectrometer. Excitation at 1064 nm was provided by a Nd:YVO$_4$ laser with a power of 400 mW at the sample position. 1200 scans were recorded at 4 cm$^{-1}$ resolution. The FT-Raman spectrum (FIG. 2) shows bands at 215, 252, 293, 304, 315, 338, 556, 705, 858, 997, 1025, 1098, 1154, 1363, 1382, 1397, 1566, 1584, 1606 and 3059 cm$^{-1}$.

The X-Ray Powder Diffractogram pattern of the product (FIG. 3) was recorded using the following acquisition conditions: Unground material was packed into top-filled Si cups. Powder patterns were obtained using a Bruker D8 Advance X-Ray powder diffractometer configured with a Cu anode (40 kV, 40 mA), variable divergence slit, primary and secondary Soller slits, and a position sensitive detector. Data were acquired over the range 2-40 degrees 2-theta using a step size of 0.0145 degrees 2-theta (1 s per step). Samples were rotated during data collection. Characteristic 2θ XRPD angles are 6.84, 8.61, 10.47, 13.01, 15.11, 15.50, 16.24, 16.63, 17.20, 18.00, 19.65, 21.07, 21.66, 22.20, 22.62, 23.99, 25.61, 26.12, 26.76, 27.96, 28.86, 29.64, 30.26, 30.85, 31.31, 32.60, 33.08, 33.70, 34.35, 35.65, 36.85, 38.05 and 38.46°.

Example 45

Crystallisation of 3-phenylsulfonyl-8-piperazin-1-yl-quinoline (Form II)

3-Phenylsulfonyl-8-piperazin-1-yl-quinoline (E16) (0.5 g) was dissolved in isopropanol (5 ml) with warming. The solution was allowed to cool to ambient then stirred overnight before cooling in an ice-water bath for 15 min. The product was collected by filtration, and dried in vacuo at 50° C. to give the title compound, 371 mg, 74%. Melting point 164° C.

Characterising data recorded for Example 45:

The infrared spectrum was recorded using a Nicolet Avatar 360 FT-IR spectrometer fitted with a universal ATR accessory. The FT-IR spectrum (FIG. 4) shows bands at: 3335, 2939, 2812, 1585, 1564, 1485, 1470, 1443, 1382, 1361, 1322, 1310, 1250, 1232, 1179, 1158, 1129, 1107, 1093, 1061, 1022, 1000, 950, 914, 862, 813, 774, 760, 727 cm$^{-1}$ The FT-Raman spectrum of a sample in a glass tube was acquired using a ThermNicolet 960 E.S.P. spectrometer. Excitation at 1064 nm was provided by a Nd:YVO$_4$ laser with a power of 400 mW at the sample position. 1200 scans were recorded at 4 cm$^{-1}$ resolution. The FT-Raman spectrum (FIG. 5) shows bands at 216, 252, 288, 617, 701, 726, 863, 1000, 1026, 1078, 1153, 1197, 1339, 1360, 1381, 1396, 1445, 1564, 1584, and 3052 cm$^{-1}$.

The X-Ray Powder Diffractogram pattern (FIG. 6) was recorded using the following acquisition conditions: Unground material was packed into top-filled Si cups. Powder patterns were obtained using a Bruker D8 Advance X-Ray powder diffractometer configured with a Cu anode (40 kV, 40 mA), variable divergence slit, primary and secondary Soller slits, and a position sensitive detector. Data were acquired over the range 2-40 degrees 2-theta using a step size of 0.0145 degrees 2-theta (1 s per step). The sample was rotated during data collection. Characteristic 2θ XRPD angles are 9.30, 9.95, 10.99, 13.40, 14.63, 15.03, 16.04, 16.47, 17.93, 18.19, 18.73, 19.17, 20.69, 21.49, 22.12, 23.55, 24.59, 25.27, 27.03, 28.22, 28.61, 29.48, 29.81, 30.70, 32.05, 33.32, 33.95, 34.39, 34.90, 35.77, 36.25, 36.80, 37.60, 38.19, 38.70 and 39.26°.

Pharmacological Data

Compounds can be tested following the procedures outlined in WO98/27081. The compounds of Examples E1-E14, E16-34 and E37-43 were tested and showed good affinity for the 5-HT$_6$ receptor, having pKi values>8.0 at human cloned 5-HT$_6$ receptors. The compounds of examples E15 and E35-36 were also tested and showed good affinity for the 5-HT$_6$ receptor, having pKi values 7.5 at human cloned 5-HT$_6$ receptors.

The invention claimed is:

1. A method of treating a patient suffering from a disorder selected from anxiety and depression, which method comprises administering a therapeutically effective amount of a compound of formula (I):

wherein:
R$^1$ represents hydrogen, methyl, ethyl, isopropyl, isobutyl or 2,2-dimethylpropyl;
R$^2$ represents hydrogen or methyl or is linked to R$^1$ to form a group (CH$_2$)$_3$;
R$^3$ represents hydrogen, methyl or halogen;
R$^4$ and R$^5$ independently represent hydrogen, or methyl;
m represents 1 or 2, or m is 2 and both R$^2$ groups are linked to form a CH$_2$ group linking C-2 and C-5 of the piperazine ring;
n represents 1;
p represents 1 or 2;
A represents a group —Ar$^1$ wherein Ar$^1$ represents unsubstituted phenyl or phenyl substituted by halogen, cyano, C$_{1-6}$alkyl, C$_{1-6}$alkoxy, trifluoromethyl or trifluoromethoxy,
or a pharmaceutically acceptable salt thereof,
to a patient in need thereof.

2. The method according to claim 1, wherein the disorder is anxiety.

3. The method according to claim 1, wherein the disorder is depression.

4. The method according to claim 1, wherein:
$R^1$ represents hydrogen or methyl;
$R^2$ represents hydrogen or methyl;
$R^3$ represents hydrogen or halogen;
m represents 1;
n represents 1;
p represents 1;
A represents a group —$Ar^1$ wherein $Ar^1$ represents unsubstituted phenyl or phenyl substituted by halogen, cyano, trifluoromethyl or trifluoromethoxy.

5. The method according to claim 1, wherein the compound is 3-phenylsulfonyl-8-piperazin-1-yl-quinoline or a pharmaceutically acceptable salt thereof.

6. The method according to claim 1, wherein the compound is the free base of 3-phenylsulfonyl-8-piperazin-1-yl-quinoline.

7. The method according to claim 2, wherein the compound is 3-phenylsulfonyl-8-piperazin-1-yl-quinoline or a pharmaceutically acceptable salt thereof.

8. The method according to claim 2, wherein the compound is the free base of 3-phenylsulfonyl-8-piperazin-1-yl-quinoline.

9. The method according to claim 3, wherein the compound is 3-phenylsulfonyl-8-piperazin-1-yl-quinoline or a pharmaceutically acceptable salt thereof.

10. The method according to claim 3, wherein the compound is the free base of 3-phenylsulfonyl-8-piperazin-1-yl-quinoline.

* * * * *